United States Patent
Bernauer et al.

[11] Patent Number: 4,820,734
[45] Date of Patent: Apr. 11, 1989

[54] PHENETHYLAMINE DERIVATIVES

[75] Inventors: Karl Bernauer, Oberwil; Hans Bruderer, Biel-Benken, both of Switzerland

[73] Assignee: Hoffmann-La Roche Inc., Nutley, N.J.

[21] Appl. No.: 117,190

[22] Filed: Nov. 4, 1987

Related U.S. Application Data

[63] Continuation of Ser. No. 649,349, Sep. 11, 1984, abandoned.

[30] Foreign Application Priority Data

Sep. 15, 1983 [CH] Switzerland .................. 5032/83
Jul. 4, 1984 [CH] Switzerland .................. 3231/84

[51] Int. Cl.⁴ .................................. A61K 31/135
[52] U.S. Cl. .................... 514/649; 564/336; 564/338; 564/339; 564/304
[58] Field of Search .................. 564/336; 514/649

[56] References Cited

U.S. PATENT DOCUMENTS 4,017,637  4/1977  Yardley et al.
4,535,189  8/1985  Husbands et al. .............. 564/336

Primary Examiner—Richard L. Raymond
Assistant Examiner—A. A. Owens
Attorney, Agent, or Firm—Jon S. Saxe; Bernard S. Leon; Richard J. Mazza

[57] ABSTRACT

The novel phenethylamine derivatives of the general formula

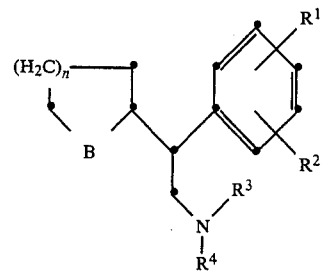

wherein $R^1$ and $R^2$ each signify hydrogen, halogen, trifluoromethyl, lower alkoxy, lower alkyl, hydroxy or nitro, with the proviso that at least one of $R^1$ and $R^2$ is different from hydrogen, $R^3$ and $R^4$ each signify lower alkyl, n signifies the number 1, 2, 3 or 4 and B signifies the group —CO— or —CHOH—, and their pharmaceutically acceptable acid addition salts have interesting analgesic and antidepressant properties. These substances can be manufactured according to various methods which are known per se and can be used as medicaments in the form of pharmaceutical preparation.

30 Claims, No Drawings

PHENETHYLAMINE DERIVATIVES

This is a continuation, of application Ser. No. 649,349 filed Sept. 11, 1984 now abandoned.

DETAILED DESCRIPTION OF THE INVENTION

The present invention is concerned with novel phenethylamine derivatives with valuable pharmacodynamic properties. In particular, it is concerned with compounds of the general formula

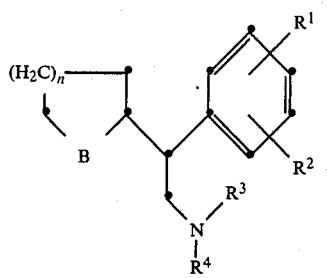

wherein $R^1$ and $R^2$ each signify hydrogen, halogen, trifluoromethyl, lower alkoxy, lower alkyl, hydroxy or nitro, with the proviso that at least one of $R^1$ and $R^2$ is different from hydrogen, $R^3$ and $R^4$ each signify lower alkyl, n signifies the number 1, 2, 3 or 4 and B signifies the group —CO— or —CHOH—, and pharmaceutically acceptable acid addition salts thereof.

Objects of the present invention are the compounds of formula I above and their pharmaceutically acceptable acid addition salts per se and as pharmaceutically active substances, the manufacture of these compounds and intermediates for their manufacture, medicaments containing such a compound and the manufacture of such medicaments, as well as the use of these compounds in the control or prevention of illnesses.

The term "lower" in combinations such as "lower alkyl", "lower alkyl group", "lower alkoxy" and the like denotes residues with at most 4 cabon atoms. The term "alkyl" denotes straight-chain or branched, saturated hydrocarbon residues such as methyl, ethyl, isopropyl and the like. The term "alkoxy" denotes alkyl groups linked via an oxygen atom such as e.g. methoxy, ethoxy, isopropoxy and the like. The term "halogen" signifies fluorine, chlorine, bromine or iodine.

The compounds of formula I defined above have two asymmetrically substituted carbon atoms or, when B signifies the group —CHOH—, three asymmetrically substituted carbon atoms. The present invention embraces not only the optically uniform forms of these compounds, but also the various diastereosomeric racemates and mixtures of different diastereoisomeric racemates.

The diastereoisomeric racemates with the relative configuration depicted in general formula Ia or Ib, as well as the corresponding optically uniform enantiomeric forms are especially preferred:

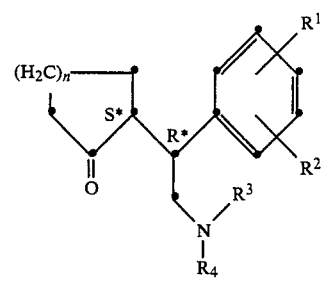

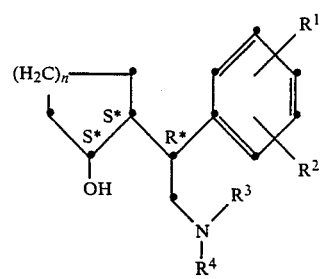

wherein $R^1$, $R^2$, $R^3$, $R^4$ and n have the above significance.

In a preferred embodiment, the present invention embraces compounds of formula I in which either $R^1$ signifies halogen, lower alkoxy or hydroxy and $R^2$ signifies hydrogen or $R^1$ and $R^2$ in each case both signify halogen, lower alkoxy or hydroxy. The term "halogen" preferably signifies chlorine and the term "lower alkoxy" preferably signifies methoxy. Especially preferred are those compounds of formula I in which $R^1$ signifies chlorine or hydroxy and $R^2$ signifies hydrogen, chlorine or hydroxy, and especially those in which $R^2$ signifies hydrogen and $R^1$ is present in the 4-position of the phenyl ring and signifies chlorine or hydroxy or $R^1$ is present in the 3-position of the phenyl ring and signifies hydroxy. Preferably, n singifies the number 2. B preferably signifies the group —CHOH—. $R^3$ and $R^4$ preferably stand for methyl.

Quite especially preferred compounds in the scope of the present invention are:

rac-(1S*)-cis-2/(R*)-4-Chloro-α-[(dimethylamino)-methyl]benzyl/cyclohexanol and rac-(1S*)-cis-2-(R*)-α-[(dimethylamino)methyl]-4-hydroxybenzyl/cyclohexanol.

Further especially preferred compounds are:

(1S)-cis-2-/(R)-4-Chloro-α-[(dimethylamino)methyl]-benzyl/cyclohexanol.

(1R)-cis-2-/(S)-4-chloro-α-[(dimethylamino)methyl]-benzyl/cyclohexanol.

rac-(1S*)-cis-2-/(R*)-3,4-dichloro-α-[(dimethylamino)-methyl]benzyl/cyclohexanol.

rac-(1S*)-cis-2-/(R*)-4-methoxy-α-[(dimethylamino)-methyl]benzyl/cyclohexanol.

rac-(1S*)-cis-2-/(R*)-α-[(dimethylamino)methyl[-3,4-dimethoxybenzyl/cyclohexanol.

rac-(2S*)-2-/(R*)-4-chloro-α-[(dimethylamino)methyl]-benzyl/cyclohexanone and (1S)-cis-2-/(R)-α-[(dimethylamino)methyl]-4-hydroxy-benzyl/cyclohexanol.

The compounds of formula I and their pharmaceutically acceptable acid addition salts can be manufactured in accordance with the invention by (a) di-alkylating or mono-alkylating the primary or secondary amino group in a compound of the general formula

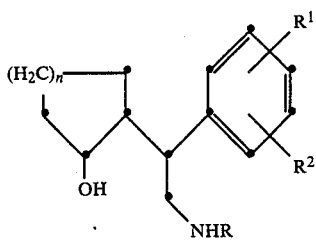

wherein $R^1$, $R^2$ and n have the above significance and R signifies hydrogen or lower alkyl. or (b) oxidizing the secondary alcohol grouping in a compound of the general formula

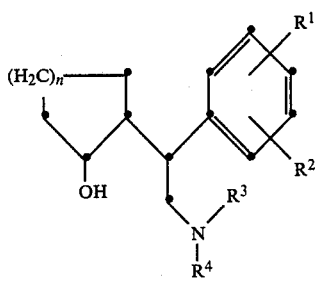

wherein $R^1$, $R^2$, $R^3$, $R^4$ and n have the above significance, or (c) cleaving off the protecting group(s) from a compound of the general formula

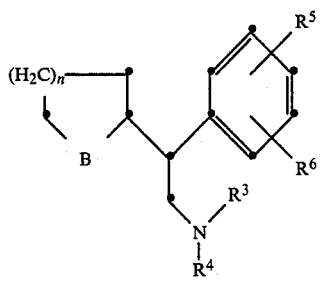

wherein $R^3$, $R^4$, n and B have the above significance and one of the residues $R^5$ and $R^6$ signifies a protected hydroxyl group and the other signifies hydrogen, halogen, trifluoromethyl, lower alkoxy, lower alkyl, nitro or a protected hydroxyl group, or (d) nitrating a compound of the general formula

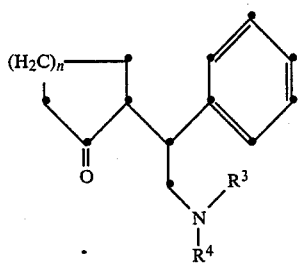

wherein $R^3$, $R^4$ and n have the above significance, in the p-position of the phenyl ring, and, if desired, (e) separating a mixture of different racemates obtained into the racemates, (f) resolving a racemate obtained into the optical antipodes and/or (g) converting a compound of formula I obtained into a pharmaceutically acceptable acid addition salt.

In accordance with process (a) there are manufactured compounds of formula I in whcih B singifies the group —CHOH— and $R^1$, $R^2$, $R^3$, $R^4$ and n have the significance mentioned earlier. For the N-alkylatin there come into consideration variour methods which are known per se and which are familiar to any person skilled in the art. For example, a compound of formula II can be reacted with an alkyl halide such as methyl iodide or with a dialkuyl sulphate such as dimethyl sulphate in an inert organic solvent such as dimethylformamide, acetonitrile, tetrahydrofuran or the like and in the presence of an acid-binding agent such as potassium carbonate, triethylamine or the like. The alkylation can, however, also be carried out in two steps. In a first step the compound of formula II is reacted with a reactive carboxylic acid derivative, for example with a carboxylic acid chloride, whereupon in a second step the carboxylic acid aminde formed is reduced to the corresponding amine with a reactive complex hydride, e.g. with lithium aluminium hydride. This method is especially suitable for the alkyltion of compounds of formula II in which R signifies lower alkyl. In a preferred embodiment ther is used as the starting material a compound of formula II in which R singifies hydrogen and this is alkylated with an alhehyde such as formaldehyde in the presence of a suitable reducing agent such as formic acid. As the solvent there can be used, for example, dimethylformamide, tetrahydrofuran, 1,2-dimethoxyethane or the like. If formic acid is used as the reducing agent, then an additional solvent is not absolutely necessary. The temperature is not critical; the reaction can be carried out in a range of about room temperature to the boiling temperature of the reaction mixture.

In accordance with process (b) there are manufactured compounds of formula I in which B signifies the group —CO— and $R^1$, $R^2$, $R^3$, $R^4$ and n have the significance mentioned earlier. Various known oxidizing agents such as concentrated nitric acid, Jones' reagent, potassium permanganate or the like can be used for the oxidation of the secondary alcohol grouping in a compound of formula Ic, whereby the reaction conditions which are usual in the respective case are used. Concentrated (65 percent) nitric acid is an especially preferred oxidizing agent for the purpose of the present invention. An additional solvent is not necessary in this case. The oxidation with concentrated nitric acid is conveniently carried out at low temperature, i.e. in a range of about $-30°$ C. to $0°$ C.

In accordance with process (c) there are maufactured compounds of formula I in which $R^1$ and /or $R^2$ signify hydroxy and $R^3$, $R^4$, n and B have the significance mentioned above. As protecting groups there are suitable, of course, only those which are stable under the conditions of the preparation of the compounds of formula III described below and which can be removed selectively without other structural elements present in the molecule being affected. The choice of the protecting groups suitable for this should present no difficulties to the person skilled in the art. Especially well suited protecting groups which fulfil the above conditions are, for example, the benzyl group or benzyl groups which are substituted on the phenyl ring. Such protecting groups can be cleaved off readily by catalytic hydrogenation, for example in the presence of palladium/carbon at room temperature and atmospheric pressure.

In accordance with process (d) there are manufactured compounds of formula I in which $R^1$ singifies nitro in the p-position, $R^2$ signifies hydrogen and B singifies the group —CO—, and $R^3$, $R^4$ and n have the significance mentioned earlier. The nitration is carried out according to methods which are known per se and which are familiar to any person skilled in the art. Fuming nitric acid is preferably used as the nitrating agent for the purpose of the present invention, whereby in this case an adddditional solvent is not necessary. The nitration with fuming nitric acid is conveniently carried out at low temperatures, i.e. in a range of about —° C. to 0° C.

Depending on the stereochemistry of the starting materials used the desired products are obtained as a mixture of different racemates, as racemates or as optically uniform forms. Mixtures of different racemates can be separated by means of conventional methods, whereby fractional crystallization and column chromatography on silica gel or aluminium oxide are especially well suited. Racemates can be resolved, for example, via fractional crystallization of the diastereoisomeric ammonium salts obtained with optically active acids such as (R,R)-tartaric acid, (S,S)-tartaric acid or the like.

The manufacture of pharmaceutically acceptable acid addition salts of compounds of formula I is carried out according to generally usual methods. There come into consideration not only salts with inorganic acids but also salts with organic acids, for example hydrochlorides, hydrobromides, sulphates, methanesulphonates, p-toluenesulphonates, oxalates, tartrates and the like.

The compounds of formula II used as starting materials are novel and are likewise an object of the present invention. They can be prepared by reducing a compound of the general formula

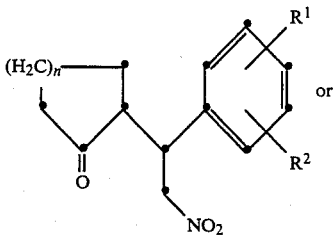

V or

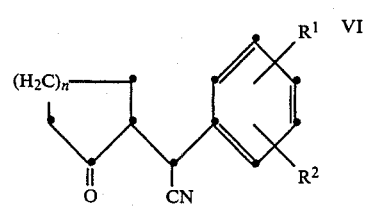

VI wherein $R^1$, $R^2$ and n have the above significance, with a reactive, complex metal hydride such as lithium aluminium hydride in an inert organic solvent such as tetrahydrofuran and, if desired, mono-alkylating the primary amino group in the resulting compound of the general formula

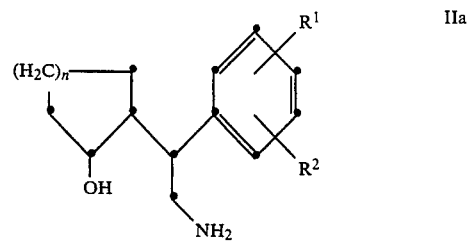

IIa wherein $R^1$, $R^2$ and n have the above significance.

This alkylation is conveniently carried out by first acylating the compound of formula IIa with a reactive carboxylic acid derivative, for example a carboxylic acid chloride, and then reducing the amide formed to the desired secondary amine with a reactive, complex metal hydride such as lithium aluminium hydride. If desired, resulting mixtures of diastereoisomeric racemates of compounds of formula II can be separated at this stage whereby fractional crystallization and column chromatography on silica gel or aluminium oxide are well suited for this. Of course, racemates which also may be obtained can be resolved at this stage. On the other hand, and this is especially true for the compounds of formula V, starting materials with defined stereo- chemistry can already be used for the prepartion of compounds of formula II.

The compounds of formula V are known or can be prepared in analogy to the known representatives of this class of substance by reacting a compound of the general formula

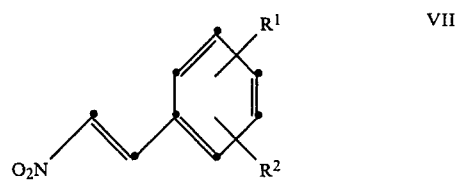

VII wherein $R^1$ and $R^2$ have the above significance, with an enamine or lithium enolate of a ($C_{5-8}$)-cycloalkonone. When ($C_{5-8}$)-cycloalkanone are used there is obtained as the product an enamine of a compound of formula V which is then hydrolyzed to the ketone of formula V. When an optically active enamine, which can be obtained by reacting an optically active secondary amine such as (R)-2-methoxymethyl-pyrrolidine with a ($C_{5-8}$)-cycloalkanone, is used, then optically active compounds of formula V can be obtained in high optical yield.

The compounds of formula VI can be presented by reacting a compound of the general formula

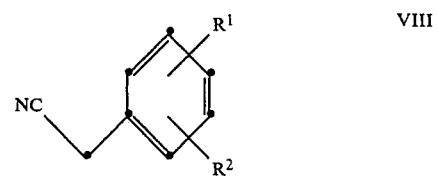

VIII wherein R¹ and R² have the above significance, in a manner known per se in the presence of a strong base with a compound of the general formula

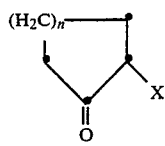

wherein X signifies a halogen atom and n has the above significance.

The compounds of formula III are novel and are likewise an object of the present invention. They can be prepared by di-alkylating or mono-alkylating the primary or secondary amino group in a compound of the general formula

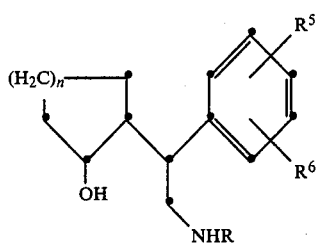

wherein $R^5$, $R^6$, R and n have the above significance, in a manner known per se and, if desired, oxidizing the secondary alcohol grouping in the compound obtained. The alkylation is preferably carried out with an aldehyde such as formaldehyde in the presence of a reducing agent such as formic acid and the oxidation is preferably carried out with concentrated nitric acid (65 percent).

The compounds of formula X can be prepared similarly to the compounds of formula II, namely starting from compounds of formula VII or VIII in which, however, R¹ and R² have the significances given above for $R^5$ and $R^6$.

mary or secondary amino group in a compound of the general formula

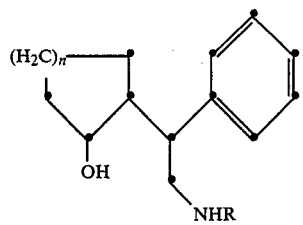

wherein R and n have the above significance, in a manner known per se and subsequently oxidizing the secondary alcohol grouping in the compound obtained. The alkylation is preferably carried out with an aldehyde such as formaldehyde in the presence of a reducing agent such as formic acid and the oxidation is preferably carried out with concentrated nitric acid (65 percent).

The compounds of formula XI can be prepared similarly to the compounds of formula II, namely starting from compounds of formula VII or VIII in which, however, R¹ and R² signifiy hydrogen.

As already mentioned earlier, the compounds of formula I and their pharmaceutically acceptable acid addition salts have valuable pharmacodynamic properties. In particular, they have interesting analgesic, antidepressant and acute inflammation-inhibiting properties. The analgesic activity can be demonstrated in the writhing test on the mouse, which is known and recognized by specialists in the field, and the antidepressant activity can be demonstrated in the known serotonin-uptake test [see M. J. Kuhar et al., Journal of Pharmacology and Experimental Therapeutics 181, 36 (1972)]. In the following Table there are given the results determined in these tests for some representative members of the class of compound defined by general formula I. Moreover, the Table contains data concerning the acute toxicity of these compounds ($LD_{50}$ after single oral administration to mice).

TABLE

| Compound of formula I | Writhing Test $ED_{50}$ in mg/kg p.o. | Serotonin-uptake Test, $IC_{50}$ in nM | $LD_{50}$ in mg/kg p.o. |
|---|---|---|---|
| rac-(1S*)—cis-2-/(R*)—4-Chloro-α-[(dimethylamino)methyl]benzyl/cyclohexanol hydrochloride | 18 | 88 | 312–625 |
| rac-(1S*)—cis-2-/(R*)—α-[Dimethylamino)methyl]4-hydroxybenzyl/cyclohexanol hydrochloride | 8.4 | 180 | 500–1000 |
| (1S)—cis-2-/(R)—4-Chloro-α-[(dimethylamino)methyl]benzyl/cyclohexanol hydrochloride | 14 | 110 | 125–250 |
| (1R)—cis-2-/(S)—4-Chloro-α-[(dimethylamino)methyl]benzyl/cyclohexanol hydrochloride | 19 | 55 | 125–250 |
| rac-(1S*)—cis-2-/(R*)—3,4-Dichloro-α-[(dimethylamino)methyl]benzyl/cyclohexanol hydrochloride | 9.7 | 21 | 62.6–125 |
| rac-(1S*)—cis-2-/(R*)—4-Methoxy-α-[(dimethylamino)methyl]benzyl/cyclohexanol hydrochloride | 23 | 120 | 250–500 |
| rac-(1S*)—cis-2-/(R*)—α-[(Dimethylamino)methyl]-3,4-dimethoxybenzyl/cyclohexanol hydrochloride | 10 | 100 | 500–1000 |
| rac-(2S*)—2-/(R*)—4-Chloro-α-[(dimethylamino)methyl]benzyl/cyclohexanone hydrochloride | 22 | 240 | 156–312 |

The compounds of formula IV are novel and are likewise an object of the present invention. They can be prepared by di-alkylating or mono-alkylating the pri- As mentioned earlier, compounds of general formula I and pharmaceutically acceptable acid addition salts thereof can be used in accordance with the invention in the control or prevention of illnesses, especially in the control or prevention of pains and depressions. The dosage of the compounds of formula I and their pharmaceutically acceptable acid addition salts can vary within wide limits and should, of course, be fitted to the individual requirements in each individual case. In general, in the case of oral administration a daily dosage of 25-150 mg should be sufficient.

The compounds of formula I and their pharmaceutically acceptable acid addition salts can be used as medicaments, e.g. in the form of pharmaceutical preparations. The pharmaceutical preparations can be administered orally, e.g. in the form of tablets, coated tablets, dragees, hard gelatine capsules, soft gelatine capsules, soft gelatine capsules, solutions emulsions or suspensions. The administration can, however, also be carried out rectally, e.g. in the form of suppositories, or parenterally, e.g. in the form of injection solutions.

For the manufacture of pharmaceutical preparations the products in accordance with the invention can be processed with pharmaceutically or therapeutically inert, inorganic or organic carriers. Lactose, maize starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance. No carriers are, however, generally required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

Moreover, the pharmaceutical preparations can contain preserving agents, solubilizers, stabilizing agents, wetting agents, emulsifying agents, sweetening agents, colouring agents, flavouring agents, salts for varying the osmotic pressure, buffers, coating agents or antioxidants. The can also contain still other therapeutically valuable substances.

As mentioned earlier, medicaments containing a compound of formula I or a pharmaceutically acceptable acid addition salt thereof are likewise an object of the present invention, as is a process for the manufacture of such medicaments which comprise bringing one or more compounds of formula I or pharmaceutically acceptable acid addition salts thereof and, if desired, one or more other therapeutically valuable substances into a galenical administration form.

The following Examples are intended to illustrate the present invention in more detail, but are not intended to limit its extent in any manner. All temperatures are given in degrees Centigrade. The term "ether" stands for diethyl ether and the term "isopropyl ether" stands for "diisopropyl ether".

EXAMPLE 1

(a) A solution of 237 g (1.29 mol) of 4-chloro-ω-nitrostyrene in 1400 ml of methylene chloride is added dropwise while stirring and cooling within about 2 hours to a solution of 215.7 g (1.29 mol) of N-(1-cyclohexen-1-yl)morpholine in 600 ml of methylene chloride so that the temperature does not exceed 5°. The mixture is subsequently stirred for a further 3 hours. The mixture is treated with ice while stirring intensively and then rapidly with 710 ml of 2N hydrochloric acid solution, whereupon the mixture is stirred for a further 30 minutes. The aqueous phase is separated and extracted twice with 1 l of methylene chloride each time, the organic phase is washed twice with 500 ml of water each time, dried over magnesium sulphate and concentrated to about 300 ml. After the addition of 2 l of ether the mixture is left to stand overnight in a refrigerator. There is obtained rac-(2S*)-2-[(R*)-4-chloro-α-(nitromethyl)benzyl]-cyclohexanone in the form of colourless crystals of melting point 96°-97°.

(b) A solution of 112 g (0.4 mol) of rac-(2S*)-2-[(R*)-4-chloro-α-(nitromethyl)benzyl]cyclohexanone in 1 l of dry tetrahydrofuran is added dropwise under argon to a suspension of 39 g (1.03 mol) of lithium aluminium hydride in 1 l of dry tetrahydrofuran so that the temperature does not exceed 50°, whereupon the reaction mixture is stirred at 50° overnight. After cooling to room temperature the reaction mixture is treated with 50 ml of ethanol and subsequently with 200 ml of tetrahydrofuran/water (1:1), the separated precipitate is filtered off under suction while washing with methylene chloride and the filtrate is evaporated. The oil obtained is dissolved in 1 l of ether and the solution is left to stand at room temperature overnight. The separated colourless crystals are filtered off under suction, there being obtained rac-(1S*)-cis-2-[(R*)-α-(aminomethyl)-4-chlorobenzyl]cyclohexanol of m.p. 108°-110°. The rac-(1S*)-cis-2-[(R*)-α-(aminomethyl)-4-chlorobenzyl]cyclohexanol hydrochloride prepared from the base in the usual manner is recrystallized from ethanol/ether and melts at 259°-260° (decomposition).

(c) A solution of 37.7 g (0.15 mol) of rac-(1S*)-cis-2-[(R*)-α-(aminomethyl)-4-chlorobenzyl]cyclohexanol in 300 ml of dimethylformamide is treated with 30 ml of 37 percent formaldehyde solution and 15 ml of 88 percent formic acid and held at 100° for 3 hours. After cooling the readily volatile constituent is distilled off in a water-jet vacuum at 75°, the residue is treated with 3N sodium hydroxide solution, whereupon the mixture is extracted with methylene chloride. The organic phase is washed with water, dried over magnesium sulphate and evaporated. The colorless oil obtained is taken up in hexane. After leaving to stand at room temperature overnight the separated precipitate is filtered off under suction. There is obtained rac-(1S*)-cis-2-/(R*)-4-chloro-α-[(dimethylamino)methyl]benzyl/cyclohexanol in the form of colourless crystals of m.p. 88°-89°. the rac-(1S*)-cis-2-/(R*)-4-chloro-α-[(dimethylamino)methyl]benzyl/cyclohexanol hydrochloride prepared from the base is recrystallized from ethanol/ether. There are obtained colourless crystals of m.p. 267°-268°.

EXAMPLE 2

20.0 g (0.07 mol) of rac-(1S*)-cis-2-/(R*)-4-chloro-α-[(dimethylamino)methyl]benzyl/cyclohexanol and 5.83 g of (0.04 mol) of natural (R,R)-tartaric acid are dissolved together in 500 ml of hot ethanol and the solution is left to stand at room temperature overnight. The separated (+)-(1S)-cis-2-/(R)-4-chloro-α-[(dimethylamino)methyl]benzyl/cyclohexanol (R,R)-tartrate (1:1) is recrystallized from 100 ml of methanol, whereby colourless crystals of m.p. 178°-179° (decomposition) separate; $\alpha_D = +27.0°$ (c=1, water). The tartrate obtained is dissolved in water, the solution is made alkaline with 3N sodium hydroxide solution and the base is extracted with ether. The organic phase is washed once with water, dried over magnesium sulphate and evaporated. The crystalline product obtained is crystallized from isopropyl ether/hexane. There is obtained (−)-(1S)-cis-2-/(R)-4-chloro-α-[(dimethylamino)methyl]-benzyl/cyclohexanol of m.p. 117°–117.5°; $\alpha_D = -7.9°$ (c=1, ethanol). The (+)-(1S)-cis-2-/(R)-4-chloro-α-[(dimethylamino)methyl]benzyl/cyclohexanol hydrochloride obtained from the base in the usual manner is recrystallized from ethanol/ether and melts at 278°–279°; $\alpha_D = +24.4°$ (c=1, water).

EXAMPLE 3

The filtrate obtained in Example 2 after the separation of the crystalline R,R-tartrate is evaporated, the residue is treated with 5.83 g of unnatural (S,S)-tartaric acid and the mixture is dissolved in 100 ml of methanol at the boiling point. After cooling the mixture is treated with 50 ml of ether and left to stand at room temperature overnight. The colourless crystals obtained are recrystallized from 100 ml of hot methanol. There is obtained (−)-(1R)-cis-2-/(S)-4-chloro-α-[(dimethylamino)methyl]benzyl/cyclohexanol (S,S)-tartrate of m.p. 177°–177.5°; $\alpha_D = -26.3°$ (c=1, water). The (+)-(1R)-cis-2-/(S)-4-chloro-α-[(dimethylamino)methyl]benzyl/cyclohexanol prepared therefrom is recrystallized from isopropyl ether and melts at 115°–116°; $\alpha_D = +8.2°$ (c=1, ethanol). The (−)-(1R)-cis-2-/(S)-4-chloro-α-[(dimethylamino)methyl]benzyl/cyclohexanol hydrochloride prepared in the usual manner is recrystallized from ethanol/ether and has a m.p. of 278°–279°; $\alpha_D = -23.6°$ (c=1, water).

EXAMPLE 4

(a) A solution of 143 g (0.78 mol) of 2-chloro-ω-nitrostyrene in 800 ml of methylene chloride is added dropwise while stirring and cooling within about 1.5 hours to a solution of 130.3 g (0.78 mol) of N-(1-cyclohexen-1-yl)morpholine in 800 ml of methylene chloride under nitrogen so that the temperature does not exceed 20°. The mixture is subsequently stirred for a further 3 hours. The mixture is treated with 408 ml of 2N hydrochloric acid while stirring intensively and stirred for 30 minutes. The aqueous phase is separated and extracted twice with 500 ml of methylene chloride each time, the organic phase is washed with water, dried over magnesium sulphate and evaporated. The oily residue is treated with 500 ml of isopropyl ether, whereupon the mixture is left to stand in a refrigerator overnight. There is obtained rac-(2S*)-2-[(R*)-2-chloro-α-(nitromethyl)-benzyl]cyclohexanone in the form of colourless crystals of m.p. 107°–108°.

(b) A solution of 56.3 g (0.2 mol) of rac-(2S*)-2-[(R*)-2-chloro-α-(nitromethyl)benzyl]cyclohexanone in 500 ml of dry tetrahydrofuran is added dropwise while stirring to a suspension of 18.9 g (0.5 mol) of lithium aluminium hydride in 500 ml of dry tetrahydrofuran under argon so that the temperature does not exceed 50°. The reaction mixture is then stirred at 50° for a further 15 hours. After cooling the mixture is treated first with 50 ml of ethanol and subsequently with tetrahydrofuran/water (1:1), the separated precipitate is filtered off under suction while washing with methylene chloride and the filtrate is evaporated. The oily residue obtained is treated with 3N hydrochloric acid, whereupon the mixture is extracted twice with 250 ml of ether each time. The aqueous phase is made alkaline with 3N sodium hydroxide solution and extracted twice with 500 ml of methylene chloride each time. The organic phase is washed with water, dried over magnesium sulphate and evaporated. The crude product is obtained in the form of a yellow oil; it is converted into the hydrochloride in the usual manner. After repeated recrystallization from methylene chloride/methanol there is obtained rac-(1S*)-cis-2-[(R*)-α-(aminomethyl)-2-chlorobenzyl]cyclohexanol hydrochloride of m.p. 278°–280°.

(c) 7.6 g (30 mmol) of rac-(1S*)-cis-2-[(R*)-α-(aminomethyl)-2-chlorobenzyl]cyclohexanol are dissolved in 60 ml of dimethylformamide, whereupon the solution is treated with 30 ml of 37 percent formaldehyde solution and 15 ml of 88 percent formic acid and heated to 100° for 15 hours. After distilling off the readily volatile constituents in a water-jet vacuum at 70° the residue is treated with 3N sodium hydroxide solution. The base is extracted twice with 500 ml of ether each time. The organic phase is washed with water, dried over magnesium sulphate and evaporated. The yellow oil obtained is chromatographed on a ten-fold amount of aluminum oxide (activity grade II, neutral). By elution with 500 ml of toluene/ether (1:1) there is obtained a colourless oil which crystallizes after treatment with hexane. The rac-(1S*)-cis-2-/(R*)-2-chloro-α-[(dimethylamino)methyl]benzyl/cyclohexanol obtained melts at 60°–61°. The rac-(1S*)-cis-2-/(R*)-2-chloro-α-[(dimethylamino)methyl]benzyl/cyclohexanol hydrochloride prepared therefrom is recrystallized from ethyl acetate, there being obtained colourless crystals of m.p. 180°–180.5°.

EXAMPLE 5

(a) A solution of 52.3 g (0.24 mol) of 3,4-dichloro-ω-nitrostyrene in 500 ml of methylene chloride is added while stirring and cooling within about 45 minutes to a solution of 40.1 g (0.24 mol) of N-(1-cyclohexen-1-yl)morpholine in 400 ml of methylene chloride under nitrogen so that the temperature does not exceed 0°. The mixture is subsequently stirred at 0° for a further 3 hours. 420 ml of 1N hydrochloric acid are added rapidly while stirring intensively, whereupon the mixture is stirred for a further 30 minutes. The aqueous phase is separated and extracted twice with 500 ml of methylene chloride each time; the organic phase is washed with water, dried over magnesium sulphate and evaporated. The oily residue obtained is taken up in 250 ml of isopropyl ether and left to stand in a refrigerator overnight. There is obtained rac-(2S*)-2-[(R*)-3,4-dichloro-α-(nitromethyl)benzyl]cyclohexanone in the form of colourless crystals of m.p. 109°–110°.

(b) A solution of 28.5 g (0.09 mol) of rac-(2S*)-2-[(R*)-3,4-dichloro-α-(nitromethyl)benzyl]cyclohexanone in 500 ml of dry tetrahydrofuran is added dropwise to a suspension of 8.53 g (0.22 mol) of lithium aluminum hydride in 200 ml of dry tetrahydrofuran under argon so that temperature does not exceed 50°, whereupon the mixture is stirred at 50° for 15 hours. After cooling the reaction mixture is treated with tetrahydrofuran/water (1:1), the separated precipitate is filtered off under suction while washing with methylene chloride and the filtrate is evaporated. The thus-obtained oil is treated with 3N hydrochloric acid, whereupon the mixture is extracted twice with 500 ml of ether each time. The aqueous phase is made alkaline with 3N sodium hydroxide solution and extracted twice with 500 ml of methylene chloride each time. The organic phase is washed twice with 100 ml of water each time, dried over magnesium sulphate and evaporated. There is obtained a viscous oil which crystallizes from isopropyl ether/hexane. There is obtained rac-(1S*)-cis-2-[(R*)-α-(aminomethyl)-3,4-dichlorobenzyl]cyclohexanol in the form of colourless crystals of m.p. 117°–118°.

(c) 7.2 g (25 mmol) of rac-(1S*)-cis-2-[(R*)-α-(aminomethyl)-3,4-dichlorobenzyl]cyclohexanol are dissolved in 50 ml of dimethylformamide, treated with 25 ml of 37 percent formaldehyde solution and 12.5 ml of 88 percent formic acid and heated to 100° for 5 hours. After distilling off the readily volatile constituents in a water-jet vacuum at 70° the residue is treated with 3N sodium hydroxide solution and extracted twice with 500 ml of ether each time. The organic phase is washed with water, dried over magnesium sulphate and evaporated. The yellow oil obtained crystallizes upon treatment with isopropyl ether. There is obtained rac-(1S*)-cis-2-/(R*)-3,4-dichloro-α-[(dimethylamino)methyl]benzyl/cyclohexanol in the form of colourless crystals of m.p. 121°–122°. The rac-(1S*)-cis-2-/(R*)-3,4-dichloro-α-[(dimethylamino)methyl]benzyl/cyclohexanol hydrochloride prepared in the usual manner is recrystallized from methylene chloride/isopropyl ether and melts at 259°–260° (decomposition).

EXAMPLE 6

(a) A solution of 89.8 g (0.54 mol) of 4-fluoro-ω-nitrostyrene in 300 ml of methylene chloride is added dropwise while stirring and cooling with ice within about 85 minutes to a solution of 90.3 g (0.54 mol) of N-(1-cyclohexen-1-yl)morpholine in 500 ml of methylene chloride under nitrogen so that the temperature does not exceed 5°. The mixture is then stirred at room temperature for 4 hours, treated rapidly with 295 ml of 2N hydrochloric acid while stirring intensively and stirred for 30 minutes. The aqueous phase is separated and extracted twice with 500 ml of methylene chloride each time; the organic phase is washed with water, dried over magnesium sulphate and evaporated. The oily residue obtained is taken up in isopropyl ether and the solution is left to stand in a refrigerator overnight. There is obtained rac-(2S*)-2-[(R*)-4-fluoro-α-(nitromethyl)benzyl]cyclohexanone in the form of colourless crystals of m.p. 84°–85°.

(b) A solution of 105 g (0.4 mol) of rac-(2S*)-2-[(R*)-4-fluoro-α-(nitromethyl)benzyl]cyclohexanone in 1 l of dry tetrahydrofuran is added dropwise while stirring to a suspension of 38 g (1 mol) of lithium aluminum hydride in 500 ml of dry tetrahydrofuran under argon so that the temperature does not exceed 50°. The reaction mixture is stirred at 50° for 15 hours, cooled and then treated with tetrahydrofuran/water (1:1). The separated precipitate is filtered off under suction while washing with methylene chloride and the filtrate is distilled. The oil obtained is treated with 3N hydrochloric acid, extracted twice with 500 ml of ether each time, the aqueous phase is made alkaline with ammonia and extracted with ether. The organic phase is washed with water, dried over magnesium sulphate and evaporated. The oil obtained is dissolved in 250 ml of isopropyl ether, whereupon the solution is left to stand in a refrigerator overnight for crystallization. There is obtained rac-(1S*)-cis-2-[(R*)-α-(aminomethyl)-4-fluorobenzyl]cyclohexanol in the form of colourless crystals of m.p. 75°–76°. The rac-(1S*)-cis-2-[(R*)-α-(aminomethyl)-4-fluorobenzyl]cyclohexanol hydrochloride prepared in the usual manner is recrystallized from ethanol/ether; there are obtained colourless crystals of m.p. 233°–234°.

(c) 7.1 g (30 mmol) of rac-(1S*)-cis-2-[(R*)-α-(aminomethyl-4-fluorobenzyl]cyclohexanol are dissolved in 60 ml of dimethylformamide, whereupon the solution is treated with 30 ml of 35 percent formaldehyde solution and 15 ml of 88 percent formic acid and stirred at 100° for 3 hours. After distilling off the readily volatile constituents in a water-jet vacuum at 75° the residue is treated with 3N sodium hydroxide solution and extracted with ether. The organic phase is washed with water, dried over magnesium sulphate and evaporated. The oil obtained crystallizes after treatment with hexane and there is obtained rac-(1S*)-cis-2-/(R*)-4-fluoro-α-[(dimethylamino)methyl]benzyl/cyclohexanol in the form of colourless crystals of m.p. 72°–73°. The hydrochloride prepared in the usual manner is recrystallized from ethanol/ether, there being obtained colourless crystals of m.p. 240°–241°.

EXAMPLE 7

(a) A solution of 17.9 g (0.1 mol) of 3-methoxy-ω-nitrostyrene in 80 ml of acetonitrile is added dropwise while stirring at −20 to a solution of 16.7 g (0.1 mol) of N-(1-cyclohexen-1-yl)morpholine in 50 ml of acetonitrile under nitrogen, whereupon the mixture is stirred at room temperature for a further 3 hours. After distilling off the solvent the residue is treated with 360 ml of 10 percent hydrochloride acid, stirred at room temperature for 2 hours, the separated precipitate is filtered off under suction and taken up in methylene chloride. The organic phase is washed with water, dried over magnesium sulphate and evaporated. The crystalline residue is recrystallized from methylene chloride/hexane, there being obtained rac-(2S*)-2-[(R*)-3-methoxy-α-(nitromethyl)benzyl]cyclohexanone in the form of colourless crystals of m.p. 125°–126°.

(b) A solution of 41.6 g (0.15 mol) of rac-(2S*)-2-[(R*)-3-methoxy-α-(nitromethyl)benzyl]cyclohexanone in 400 ml of dry tetrahydrofuran is added dropwise to a suspension of 14.2 g (0.38 mol) of lithium aluminum hydride in 400 ml of dry tetrahydrofuran under argon. The reaction mixture is then heated to boiling under reflux for 4 hours, treated, after cooling, firstly with 50 ml of ethanol, and subsequently with tetrahydrofuran/water (1:1), treated with 80 g of potassium carbonate and stirred for 30 minutes. The separated precipitate is filtered off under suction while washing with methylene chloride and the filtrate is evaporated. The residue is treated with 3N hydrochloric acid and extracted twice with 250 ml of ether each time. The aqueous phase is made alkaline with 3N sodium hydroxide solution and extracted twice with 500 ml of ether each time. The organic phase is washed twice with 50 ml of sodium chloride solution each time, dried over magnesium sulphate and evaporated. The crude product obtained as a yellowish oil is converted into the oxalate which is recrystallized from acetone. The rac-(1S*)-cis-2-[(R*)-α-(aminomethyl)-3-methoxybenzyl]cyclohexanol oxalate (2:1) obtained melts at 210°212°.

(c) 2.5 g (10 mmol) of rac-(1S*)-cis-2-[(R*)-α-(aminomethyl)-3-methoxybenzyl]cyclohexanol (obtained from the oxalate) are dissolved in 20 ml of dimethylformamide, treated with 2 ml of 35 percent formaldehyde solution and 1 ml of 88 percent formic acid and heated to 100° for 2 hours. After cooling the mixture is treated with 3N sodium hydroxide solution and extracted three times with 50 ml of ether each time. The ethereal solution is extracted with 1N hydrochloric acid and the aqueous phase is made alkaline by the addition of 3N sodium hydroxide solution. The mixture is extracted three times with 100 ml of methylene chloride each time, the organic phase is washed with sodium chloride solution, dried over magnesium sulphate and evaporated. The oil obtained is chromatographed on a 20-fold amount of aluminium oxide (activity grade II, neutral) while eluting with toluene. There is obtained rac-(1S*)-cis-2-/(R*)-3-methoxy-α-[(dimethylamino)-methyl]benzyl/cyclohexanol in the form of a colourless oil which is converted into rac-(1S*)-cis-2-/(R*)-3-methoxy-α-[(dimethylamino)methyl]benzyl/cyclohexanol hydrochloride in the usual manner. By recrystallization from ethanol/ether there are obtained colourless crystals of m.p. 188°-189°.

EXAMPLE 8

(a) A solution of 87.3 g (0.34 mol) of 3-benzyloxy-ω-nitrostyrene in 320 ml of methylene chloride is added dropwise within about 2 hours while stirring and cooling to a solution of 56.8 g (0.34 mol) of N-(1-cyclohex-en-1-yl)morpholine in 160 ml of methylene chloride under nitrogen so that the temperature does not exceed 0°. The mixture is stirred at 0° to 5° for a further 2 hours, treated with 445 ml of 1N hydrochloric acid in one portion while stirring intensively and stirred for a further 1 hour. The aqueous phase is separated and extracted twice with 500 ml of methylene chloride each time; the organic phase is washed three times with 250 ml of water each time, dried over magnesium sulphate and evaporated. The oily residue obtained is dissolved in 200 ml of methylene chloride, whereupon the solution is treated with 1 l of isopropyl ether and left to stand in a refrigerator overnight. There is obtained rac-(2S*)-2-[(R*)-3-(benzylooxy)-α-(nitromethyl)benzyl]cyclohexanone in the form of colourless crystals of m.p. 119°-120°.

(b) A solution of 106.6 g (0.3 mol) of rac-(2S*)-2-[(R*)-3-(benzyloxy)-α-(nitromethyl)benzyl]cyclohexanone in 500 ml of dry tetrahydrofuran is added drowpise while stirring within about 3 hours to a suspension of 28.6 g (0.75 mol) of lithium aluminium hydride in 500 ml of dry tetrahydrofuran under argon so that the temperature does not exceed 55°. The reaction mixture is stirred at 50° overnight, treated, after cooling, with 40 ml of ethanol and subsequently with 200 ml of tetrahydrofuran/water (1:1), the separated precipitate is filtered off under suction while washing with methylene chloride and the filtrate is evaporated. The residue is crystallized from methylene chloride/isopropyl ether, there being obtained rac-(1S*)-cis-2-[(R*)-α-(aminomethyl)-3-(benzyloxy)benzyl]cyclohexanol in the form of colourless crystals of m.p. 139°-141°.

(c) A solution of 28.4 g (87.3 mmol) of rac-(1S*)-cis-2-[(R*)-α-(aminomethyl-3-(benzyloxy)benzyl]cyclohexanol in 175 ml of dimethylformamide is treated with 17.7 ml of 37 percent formaldehyde solution and 8.8 ml of 88 percent formic acid and stirred at 100° for 3 hours. After distilling off the readily volatile constituents in a water-jet vacuum at 75° the residue is treated with 3N sodium hydroxide solution, whereupon the mixture is extracted with ether. The organic phase is washed with water, dried over magnesium sulphate and evaporated. The oil obtained is chromatographed on a 10-fold amount of aluminium oxide (activity grade II, neutral) while eluting with toluene. The oil which is thereby obtained is dissolved in hexane, wherupon the solution is left to stand in a refrigerator overnight for crystallization. There is obtained rac-(1S*)-cis-2-/(R*)-3-(benzyloxy)-α-[(dimethylamino)methyl]benzyl/cyclohexanol in the form of colourless crystals of m.p. 85°-86°.

(d) A solution of 5.0 g (14.3 mmol) of rac-(1S*)-cis-2-/(R*)-3-(benzyloxy)-α-(dimethylamino)methyl]benzyl/cyclohexanol in 50 ml of ethanol is treated with 0.5 g of 5 percent palladium/carbon and hydrogenated at room temperature. After separating the catalyst the solvent is distilled off and the crystalline residue is recrystallized from methylene chloride/isopropyl ether. There is obtained rac-(1S*)-cis-2-/(R*)-α-[(dimethylamino)methyl]-3-hydroxybenzyl/cyclohexanol in the form of colourless crystals of m.p. 171°-173°. The rac-(1S*)-cis-2-/(R*)-α-[(dimethylamino)methyl]-3-hydroxylbenzyl/cyclohexanol hydrochloride prepared therefrom in the usual manner is recrystallized from ethanol/ethyl acetate; there are obtained colourless crystals of m.p. 191°-193°.

EXAMPLE 9

(a) A solution of 142 g (0.51 mol) of 2S*)-2-[(R*)-4-methoxy-α-nitromethyl)benzyl]cyclohexanone in 1200 ml of dry tetrahydrofuran is added dropwise while stirring to a suspension of 47.5 g (1.25 mol) of lithium aluminum hydride in 1 l of dry tetrahydrofuran so that the temperature does not exceed 50°. The reaction mixture is subsequently stirred at 50° overnight, cooled to room temperature, treated with tetrahydrofuran/water (1:1), the separated precipitate is filtered off under suction while washing with methylene chloride and the filtrate is evaporated. The yellow oil obtained is dissolved in isopropyl ether, whereupon the solution is treated with hexane until it is turbid and left to stand in a refrigerator overnight. There is obtained rac-(1S*)-cis-2-[(R*)-α-(aminomethyl)-4-methoxybenzyl)cyclohexanol of m.p. 79°-81°. The rac-(1S*)-cis-2-[(R*)-α-(aminomethyl)-4-methoxybenzyl]cyclohexanol hydrochloride prepared in the usual manner is recrystallized from ethanol/ether and then melts at 216°-218°.

(b) A solution of 7.5 g (30 mmol) of rac-(1S*)-cis-2-[(R*)-α-(aminomethyl)-4-methoxybenzyl]cyclohexanol in a mixture of 60 ml of dimethylformamide, 30 ml of 35 percent formaldehyde solution and 15 ml of 88 percent formic acid is stirred at 100° for 2 hours, the readily volatile constituents are distilled off in a water-jet vacuum at 70°, the residue is treated with 3N sodium hydroxide solution and extracted with ether. The organic phase is washed with water, dried over magnesium sulphate and evaporated. The oil obtained is chromatographed on a 10-fold amount of aluminium oxide (activity grade II, neutral) while eluting with 500 ml of toluene/ether (1:1), there being obtained a colourless oil which crystallizes upon treatment with hexane. There is obtained rac-(1S*)-cis-2-/(R*)-4-methoxy-α-[(dimethylamino)methyl]benzyl/cyclohexanol in the form of colourless crystals of m.p. 69°-70°. The rac-(1S*)-cis-2-/(R*)-4-methoxy-α-[(dimethylamino)methyl]benzyl/cyclohexanol hydrochloride prepared in the usual manner is recrystallized from ethanol/ether; there are obtained colourless crystals of m.p. 199°-200°.

EXAMPLE 10

(a) A solution of 134.9 g (0.53 mol) of 4-benzyloxy-ω-nitrostyrene in 500 ml of methylene chloride is added dropwise while stirring and cooling within about 2 hours to a solution of 115 g (1 mol) of N-(1-cyclohexen-1-yl)morpholine in 250 ml of methylene chloride under nitrogen so that the temperature does not exceed 5°. The mixture is then stirred at 5° for 3 hours, treated rapidly with 580 ml of 1N hydrochloric acid while stirring intensively and stirred for a further 1 hour. The aqueous phase is separated and extracted twice with 500 ml of methylene chloride each time; the organic phase is washed three times with 200 ml of water each time, dried over magnesium sulphate and concentrated to about 300 ml. After treatment with 500 ml of isopropyl ether the mixture is left to stand in a refrigerator overnight. There is obtained rac-(2S*)-2-[(R*)-4-(benzyloxy)-α-(nitromethyl)benzyl]cyclohexanone in the form of colourless crystals of m.p. 143°–144°.

(b) A solution of 106.6 g (0.33 mol) of rac-(2S*)-2-[(R*)-4-(benzyloxy)-α-(nitromethyl)benzyl]cyclohexanone in 500 ml of dry tetrahydrofuran is added dropwise while stirring to a suspension of 28.6 g (0.75 mol) of lithium aluminium hydride in 500 ml of dry tetrahydrofuran under argon so that the temperature does not exceed 50°. The reaction mixture is stirred at 50° overnight and it is treated, after cooling to room temperature, with 300 ml of ethanol and subsequently with 100 ml of tetrahydrofuran/water (1:1). The separated precipitate is filtered off under suction while washing with methylene chloride and the filtrate is evaporated. The crystalline product obtained is recrystallized from methylene chloride/isopropyl ether. There is obtained rac-(1S*)-cis-2-[(R*)-α-(aminomethyl)-4-(benzyloxy)-benzyl]cyclohexanol in the form of colourless crystals of m.p. 160°–161°.

(c) A solution of 31.4 g (96.5 mmol) of rac-(1S*)-cis-2-[(R*)-α-(aminomethyl)-4-(benzyloxy)benzyl]cyclohexanol in 200 ml of dimethylformamide is treated with 19.3 ml of 37 percent formaldehyde solution and 9.7 ml of 88 percent formic acid and held at 100° for 3.5 hours. After distilling off the readily volatile constituents in a water-jet vacuum at 70° the residue is treated with 3N sodium hydroxide solution and extracted with methylene chloride. The organic phase is washed with water, dried over magnesium sulphate and evaporated. The oil obtained is taken up in a small amount of methylene chloride, treated with isopropyl ether and left to stand in a refrigerator overnight. There is obtained rac-(1S*)-cis-2-[(R*)-4-benzyloxy)-α-[(dimethylamino)methyl]-benzyl]cyclohexanol of m.p. 123°–124°.

(d) A solution of 19.3 g (54.6 mmol) of rac-(1S*)-cis-2/(R*)-4-(benzyloxy)-α-[(dimethylamino)methyl]benzyl/cyclohexanol in 200 ml of ethanol is hydrogenated at room temperature after the addition of 1.9 g of 5 percent palladium/carbon. After separating the catalyst the solvent is distilled off and the crystalline residue obtained is recrystallized from ethanol. There is obtained rac-(1S*)-cis-2-/(R*)-α-[(dimethylamino)methyl]-4-hydroxybenzyl/cyclohexanol in the form of colourless crystals of m.p. 211°–212°. The hydrochloride prepared in the usual manner is recrystallized from ethanol/ethyl acetate, there being obtained colourless crystals of m.p. 201°–202°.

EXAMPLE 11

(a) A solution of 29.1 g (134 mmol) of 4-trifluoromethyl-ω-nitrostyrene in 175 ml of methylene chloride is added dropwise while cooling and stirring within about 45 minutes to a solution of 29.9 g (159 mmol) of N-(1-cyclohexen-1-yl)morpholine in 60 ml of methylene chloride under nitrogen so that the temperature does not exceed 5°. The mixture is subsequently stirred for 2 hours. While stirring intensively there are then added rapidly, after the addition of ice, 170 ml of 1N hydrochloric acid, whereupon the mixture is stirred for a further 1 hour. The aqueous phase is separated and extracted twice with 200 ml of methylene chloride each time, and the organic phase is washed three times with 150 ml of water each time, dried over magnesium sulphate and evaporated. The residue is recrystallized from isopropyl ether. There is obtained rac-(2S*)-2-[(R*)-α-(nitromethyl)-4-(trifluoromethyl)benzyl]cyclohexanone in the form of colourless crystals of m.p. 107°–108°.

(b) A solution of 15 g (47.7 mmol) of rac-(2S*)-2-[(R*)-α-(nitromethyl)-4-(trifluoromethy)benzyl]cyclohexanone in 110 ml of dry tetrahydrofuran is added dropwise while stirring to a suspension of 4.42 g (116.5 mmol) of lithium aluminium hydride in 100 ml of dry tetrahydrofuran under argon so that the temperature does not exceed 50°. The reaction mixture is stirred at 50° overnight, cooled, treated with ethanol and subsequently with tetrahydrofuran/water (1:1), the separated precipitate is filtered off under suction while washing with methylene chloride and the filtrate is evaporated. The oily residue crystallizes upon treatment with isopropyl ether. There is obtained rac-(1S*)-cis-2-[(R*)-α-(aminomethyl)-4-trifluoromethyl)benzyl]cyclohexanol in the form of slightly reddish crystals of m.p. 103°–105°.

(c) A solution of 9.2 g (32 mmol) of rac-(1S*)-cis-2-[(R*)-α-(aminomethyl)-4-trifluoromethyl)benzyl]cyclohexanol in 65 ml of dimethylformamide is stirred at 100° for 2 hours with 6.5 ml of 35 percent formaldehyde solution and 3.5 ml of 88 percent formic acid. After distilling off the readily volatile constituents in a water-jet vacuum at 75° the residue is treated with 3N sodium hydroxide solution, whereupon the mixture is extracted twice with 250 ml of methylene chloride each time. The organic phase is washed with 50 ml of water, dried over magnesium sulphate and evaporated. The yellow oil obtained is chromatographed on a 30-fold amount of aluminium oxide (activity grade II, neutral) while eluting with toluene. From the resulting crystalline residue there is obtained, after treatment with hexane, rac-(1S*)-cis-2-/(R*)-α-[(dimethylamino)methyl]-4-(trifluoromethyl)benzyl/cyclohexanol of m.p. 105°–106°. The hydrochloride prepared therefrom in the usual manner is recrystallized from alcohol/ether; there are obtained colourless crystals of m.p. 263°.

EXAMPLE 12

(a) A solution of 50.5 g (163 mmol) of rac-(2S*)-2-[(R*)-3,4-dimethoxy-α-(nitromethyl)benzyl]cyclohexanone in 500 ml of dry tetrahydrofuran is added dropwise while stirring to a suspension of 15.4 g (407 mmol) of lithium aluminium hydride in 350 ml of dry tetrahydrofuran under argon so that the temperature does not exceed 50°. The reaction mixture is stirred at 50° overnight and treated, after cooling, firstly with ethanol and subsequently with tetrahydrofuran/water (1:1). The separated precipitate is filtered off under suction while washing with methylene chloride and the filtrate is evaporated. The oily crude product obtained is converted into the hydrochloride which is recrystallized from alcohol. There is obtained rac-(1S*)-cis-2-[(R*)-α-(aminomethyl)-3,4-dimethoxybenzyl]cyclohexanol hydrochloride of m.p. 216°–218°.

(b) A solution of 11.2 g (40.1 mmol) of rac-(1S*)-cis-2-[(R*)-α-(aminomethyl)-3,4-dimethoxybenzyl]cyclohexanol (obtained from the hydrochloride) in 80 ml of dimethylformamide is treated with 8 ml of 37 percent formaldehyde solution and 4 ml of 88 percent formic acid and stirred at 100° for 2 hours. After distilling off the readily volatile constituents in a water-jet vacuum at 70° the residue is taken up in ether. The solution is extracted with 3N hydrochloric acid, the acidic phase is made alkaline by the addition of conc. ammonia and extracted three times with 100 ml of methylene chloride each time. The organic phase is washed with water, dried over magnesium sulphate and evaporated. The oil obtained is chromatographed on a 10-fold amount of aluminium oxide (activity grade II, neutral) while eluting with toluene. The product is obtained as a colourless oil which is converted into the hydrochloride. After recrystallization from ethanol/ether there is obtained rac-(1S*)-cis-2-/(R*)-α-[(dimethylamino)methyl]-3,4-dimethoxybenzyl/cyclohexanol hydrochloride in the form of colourless crystals of m.p. 188°–190°.

EXAMPLE 13

(a) A solution of 6.8 g (121 mmol) of potassium hydroxide in 40 ml of water is added dropwise while cooling within about 30 minutes to a solution of 28.2 g (100 mmol) of rac-(2S*)-2-[(R*)-4-chloro-α-(nitromethyl)-benzyl]cyclohexanone in 200 ml of methanol so that the temperature does not exceed 5°. An ice-cold solution of 2.85 g (75 mmol) of sodium borohydride in 20 ml of water is subsequently added dropwise, whereupon the mixture is stirred at 0° for 3 hours. After treatment with 12 ml of acetic acid the solvent is distilled off. The residue obtained is treated with water, whereupon the mixture is extracted twice with 200 ml of ether each time. The organic phase is washed with water, dried over magnesium sulphate and evaporated. The oil obtained is taken up in ether/pentane, left to stand in a refrigerator and the crystalline product obtained is recrystallized from ether/hexan. There is obtained rac-(1S*)-2-[(R*)-4-chloro-α-(nitromethyl)benzyl]cyclohexanol of m.p. 82°–84°.

(b) 9.1 g (32.1 mmol) of rac-(1S*)-cis-2-[(R*)-4-chloro-α-(nitromethyl)benzyl]cyclohexanol, 16.8 g (64.2 mmol) of triphenylphosphine and 10.8 g (64.2 mmol) of p-nitrobenzoic acid are dissolved in 180 ml of tetrahydrofuran. To this solution is added dropwise with 30 minutes a solution of 11.3 g (64.2 mmol) of diethyl azodicarboxylate in 80 ml of tetrahydrofuran and the mixture is subsequently stirred at room temperature for 5 hours. After distilling off the solvent the residue obtained is chromatographed on a 30-fold amount of silica gel while eluting with toluene/hexane (1:2). By recrystallization of the product obtained from methylene chloride/hexane there is obtained rac-(1R*)-trans-2-[(R*)-4-chloro-α-(nitromethyl)benzyl]cyclohexyl p-nitrobenzoate in the form of colourless crystals of m.p. 146°–148°.

(c) A solution of 490 ml (12.1 mmol) of sodium hydroxide in 40 ml of ethanol is added dropwise to a solution of 3.5 g (8.09 mmol) of rac-(1R*)-trans-2-[(R*)-4-chloro-α-(nitromethyl)benzyl]cyclohexyl p-nitrobenzoate in 80 ml of ethanol. The mixture is stirred at room temperature for 16 hours, treated with 1 ml of acetic acid and the solvent is distilled off in a water-jet vacuum. The residue is treated with water, whereupon the mixture is extracted twice with 100 ml of ether each time. The organic phase is washed with water, dried over magnesium sulphate and evaporated. The residue is chromatographed on a 30-fold amount of silica gel and there is obtained rac-(1R*)-trans-2-[(R*)-4-chloro-α-(nitromethyl)benzyl]cyclohexanol in the form of a yellowish oil.

(d) A solution of 1.9 g (6.7 mmol) of rac-(1R*)-trans-2-[(R*)-4-chloro-α-(nitromethyl)benzyl]cyclohexanol in 30 ml of dry tetrahydrofuran is added dropwise while stirring to a suspension of 1 g of lithium aluminium hydride in 60 ml of dry tetrahydrofuran under argon, whereupon the mixture is stirred at 50° overnight. After cooling the reaction mixture is treated with tetrahydrofuran/water (1:1), the precipitate is filtered off under suction, the filtrate is evaporated, the residue is treated with water and extracted with ether. The rac-(1R*)-trans-2-[(R*)-α-(aminomethyl)-4-chlorobenzyl]cyclohexanol obtained is a colourless oil and is processed directly.

(e) A solution of 1.55 g (6.1 mmol) of rac-(1R*)-trans-2-[(R*)-α-(aminomethyl)-4-chlorobenzyl]cyclohexanol in 30 ml of dimethylformamide is treated with 1.5 ml of 35 percent formaldehyde solution and 0.8 ml of 88 percent formic acid and held at 100° for 2 hours. After cooling the solvent is distilled off at 75° in a water-jet vacuum; the residue is treated with water, whereupon the mixture is extracted with ether. The ethereal solution is extracted with 1N hydrochloric acid, the acidic phase is made alkaline with conc. ammonia and extracted with methylene chloride. The organic phase is washed with water, dried over magnesium sulphate and evaporated. There is obtained rac-(R*)-trans-2-/(R*)-4-chloro-α-[(dimethylamino)methyl]benzyl/cyclohexanol of m.p. 89°–90°. The rac-(1R*)-trans-2-/(R*)-4-chloro-α-[(dimethylamino)methyl]benzyl/cyclohexanol hydrochloride prepared therefrom in the usual manner is recrystallized from acetonitrile/ether and melts at 171°–173°.

EXAMPLE 14

The mother liquor which is obtained in Example 1(b) after separating the crystalline rac-(1S*)-cis-2-[(R*)-α-(aminomethyl)-4-chlorobenzyl]cyclohexanol is evaporated. The residue (54 g), which contains about 20% of rac-(1R*)-trans-2-[(R*)-α-(aminomethyl)-4-chlorobenzyl]cyclohexanol, is dissolved in 250 ml of dimethylformamide. The solution is treated with 49.5 ml of 35 percent formaldehyde solution 25 ml of 88 percent formic acid and held at 100° for 3 hours. The readily volatile constituents are distilled off in a water-jet vacuum at 75°, whereupon the residue is treated with 3N sodium hydroxide solution and extracted with ether. The organic phase is washed with water, dried over magnesium sulphate and evaporated. The oil obtained is chromatographed on a 30-fold amount of aluminium oxide (activity grade II, neutral) while eluting with toluene. There is obtained rac-(1R*)-trans-2-/(R*)-4-chloro-α-[(dimethylamino)methyl]benzyl/cyclohexanol as colourless crystals of m.p. 89°–90°.

EXAMPLE 15

(a) A solution of 12.0 g (214 mmol) of potassium hydroxide in 1 l of methanol is added rapidly under argon to a solution of 50.0 g (180 mmol) of rac-(2S*)-2-[(R*)-4-chloro-α-(nitromethyl)benzyl]cyclohexanone in 500 ml of methanol. The mixture is stirred at 0° for 1 hour, treated with 12.2 ml (214 mmol) of acetic acid and the solvent is distilled off in a water-jet vacuum. The residue is treated with water, extracted twice with 500 ml of ether each time, the ethereal phase is washed twice with 50 ml of water each time, dried over magnesium sulphate and evaporated. The oil obtained contains about 41% of the ketone isomeric to the starting material used. For purification it is chromatographed on 1 kg of silica gel while eluting with toluene/ethyl acetate (30:1). From the material obtained there is obtained, after recrystallization from methanol, rac-(2S*)-2-[(S*)-4-chloro-α-(nitromethyl)benzyl]cyclohexanone in the form of colourless crystals of m.p. 87°–88°.

(b) A solution of 5.0 g (17.7 mmol) of rac-(2S*)-2-[(S*)-4-chloro-α-(nitromethyl)benzyl]-cyclohexanone in 50 ml of dry tetrahydrofuran is added dropwise while stirring to a suspension of 1.7 g (44.8 mmol) of lithium aluminium hydride in 50 ml of dry tetrahydrofuran under argon. The reaction mixture is stirred at 50° overnight and treated, after cooling, with 20 ml of ethanol and subsequently with 30 ml of tetrahydrofuran/water (1:1). The mixture is treated with 100 ml of methylene chloride, the precipitate is filtered off under suction while washing with methylene chloride and the filtrate is evaporated. After treating the residue with water it is extracted with ether, the ethereal solution is shaken out with 3N hydrochloric acid solution, the acidic phase is treated with 3N sodium hydroxide solution and extracted with methylene chloride. The organic phase is washed with water, dried over magnesium sulphate and evaporated. The resulting oil contains about 74% of the equatorial alcohol and about 19% of the axial alcohol. By chromatography on silica gel with methylene chloride/methanol (10:1) there is isolated firstly the axial alcohol rac-(1S*)-cis-2-[(S*)-α-(aminomethyl)-4-chlorobenzyl]cyclohexanol and then the equatorial alcohol rac-(1R*)-trans-2-[(S*)-α-(aminomethyl)-4-chlorobenzyl]cyclohexanol. By recrystallization of the axial alcohol from methanol/ether there is obtained rac-(1S*)-cis-2-[(S*)-α-(aminomethyl)-4-chlorobenzyl]-cyclohexanol in the form of colourless crystals of m.p. 153°–154°.

The equatorial alcohol rac-(1R*)-trans-2-[(S*)-α-(aminomethyl)-4-chlorobenzyl]cyclohexanol is obtained in the form of colourless crystals of m.p. 138°–139°.

(c) A solution of 2.8 g (11.0 mmol) of rac-(1S*)-cis-2-[(S*)-α-(aminomethyl)-4-chlorobenzyl]cyclohexanol in 50 ml of dimethylformamide is treated with 2.6 ml of 37 percent formaldehyde solution and 0.5 ml of 88 percent formic acid and held at 100° for 3 hours. After cooling the solvent is distilled off in a water-jet vacuum at 75° and the residue is treated with water. The mixture is extracted twice with 100 ml of ether each time, the organic phase is washed with water, dried over magnesium sulphate and evaporated. The crystalline product obtained is recrystallized from isopropyl ether/hexane. There is obtained rac-(1S*)-cis-2-/(S*)-4-chloro-α-[(dimethylamino)methyl]benzyl/cyclohexanol of m.p. 126°–128°. The hydrochloride obtained in the usual manner is recrystallized from ethyl acetate; there are obtained colourless crystals of m.p. 192°–193°.

EXAMPLE 16

(a) Conc. nitric acid (65%), cooled to −20° C., is treated portionwise under argon and while stirring within about 1 hour with a total of 1.4 g (5 mmol) of rac-(1S*)-cis-2-/(R*)-4-chloro-α-[(dimethylamino)methyl]benzyl/cyclohexanol and the mixture is subsequently stirred at −20° C. for 2 hours. The reaction mixture is poured on to ice-water, made alkaline by the addition of 3N sodium hydroxide solution and extracted three times with 150 ml of methylene chloride each time. The organic phase is washed with water, dried over magnesium sulphate and evaporated. The oily product obtained is converted in the usual manner into the hydrochloride which is then recrystallized from alcohol/ether. There is obtained rac-(2S*)-2-/(R*)-4-chloro-α-[(dimethylamino)methyl]benzyl/cyclohexanone hydrochloride in the form of colourless crystals of m.p. 175°–176°.

EXAMPLE 17

(a) A solution of 17.5 g (80 mmol) of rac-(1S*)-cis-2-[(R*)-α-(aminomethyl)benzyl]cyclohexanol in 170 ml of dimethylformamide is treated with 16 ml of 35 percent formaldehyde solution and 8 ml of 88 percent formic acid and held at 100° for 3 hours. After distilling off the readily volatile constituents at 75° in a water-jet vacuum the residue is treated with 3N sodium hydroxide solution. The mixture is extracted with ether, the organic phase is washed with water, dried over magnesium sulphate and evaporated. The oil obtained is chromatographed on a 10-fold amount of aluminium oxide (activity grade II, neutral) while eluting with toluene. For crystallization, the oil obtained is dissolved in isopropyl ether, whereupon the solution is treated with hexane and left to stand in a refrigerator overnight. There is obtained rac-(1S*)-cis-2-/(R*)-α-[(dimethylamino)methyl]benzyl/cyclohexanol in the form of colourless crystals of m.p. 95°–96°. The hydrochloride prepared in the usual manner is recrystallized from ethanol/ether and melts at 212°–213°.

(b) Conc. nitric acid (65%), cooled to −20° C., is heated portionwise under argon and while stirring within about 1.5 hours with a total of 4.4 g (17.8 mmol) of rac-(1S*)-cis-2-/(R*)-α-[(dimethylamino)methyl]benzyl/cyclohexanol, the reaction mixture is subsequently stirred at −20° for a further 2 hours, poured on to ice, made alkaline by the addition of 3N sodium hydroxide solution and extracted three times with 250 ml of methylene chloride each time. The organic phase is washed with water, dried over magnesium sulphate and evaporated. The crude product, which is obtained as a yellow oil, is converted into the hydrochloride which is recrystallized from methylene chloride/ether. There is obtained rac-(2S*)-2-/(R*)-α-[(dimethylamino)methyl]benzyl/cyclohexanone hydrochloride in the form of colourless crystals of m.p. 197°–198°.

(c) A total of 9.6 g (39.1 mmol) of rac-(2S*)-2-/(R*)-α-[(dimethylamino)methyl]benzyl/cyclohexanone are introduced portionwise while stirring within about 1 hour to 125 ml of fuming nitric acid, cooled to −20°, under argon, whereupon the mixture is stirred at −20° for a further 3 hours. The reaction mixture is poured on to ice. The mixture is made alkaline by the addition of conc. ammonia and extracted three times with 300 ml of methylene chloride each time. The organic phase is washed with water, dried over magnesium sulphate and evaporated. The oil obtained is chromatographed on a 10-fold amount of aluminium oxide (activity grade II, neutral) while eluting with toluene. The crude product, which is obtained as a colourless oil, is converted in the usual manner into the hydrochloride which is recrystallized from ethanol/ethyl acetate. There is obtained rac-(2S*)-2-/(R*)-α-[(dimethylamino)methyl]-4-nitrobenzyl/cyclohexanone hydrochloride as yellowish crystals of m.p. 210°–211°.

EXAMPLE 18

(a) The mother liquor obtained in Example 10(c) after separating the crystalline rac-(1S*)-cis-2-/(R*)-4-(benzyloxy)-α-[(dimethylamino)methyl]benzyl/cyclohexanol is evaporated. The residue contains about 20% of the equatorial isomeric alcohol rac-(1R*)-trans-2-/(R*)-4-[(benzyloxy)-α-[(dimethylamino)methyl]benzyl/cyclohexanol and is chromatographed on a 30-fold amount of aluminium oxide. The axial alcohol described in Example 10(c) is eluted first with toluene and then the desired equatorial alcohol is eluted with ether. After recrystallization from isopropyl ether/hexane there is obtained rac-(1R*)-trans-2-/(R*)-4-(benzyloxy)-α[(dimethylamino)methyl]benzyl/cyclohexanol in the form of colourless crystals of m.p. 98°-100°.

(b) A solution of 3.6 g (10.2 mmol) of rac-(1R*)-trans-2-/(R*)-4-(benzyloxy)-α-[(dimethylamino)methyl]benzyl/cyclohexanol in 50 ml of ethanol is treated with 0.4 g of 5 percent palladium/carbon and hydrogenated at room temperature. After separating the catalyst the solvent is distilled off and the residue is treated with hexane. There is obtained rac-(1R*)-trans-2-/(R*)-α-[(dimethylamino)methyl]-4-hydroxybenzyl/cyclohexanol in the form of colourless crystals of m.p. 201°-202°. The hydrochloride prepared in the usual manner is recrystallized from ethanol/ether and melts at 215°-216°.

EXAMPLE 19

(a) A solution of 20 g (109 mmol) of 4-chloro-ω-nitrostyrene in 300 ml of methylene chloride is added dropwise while stirring and cooling to a solution of 25.7 g (142 mmol) of N-(1-cyclohepten-1-yl)morpholine in 200 ml of methylene chloride so that the temperature does not exceed 0°. The mixture is subsequently stirred at 0° for 3 hours. 200 ml of 1N hydrochloric acid are then added in one portion while stirring intensively, whereupon the mixture is stirred at 0° for a further 1 hour. The aqueous phase is separated and extracted twice with 200 ml of ethyl acetate each time; the organic phase is washed with water, dried over magnesium sulphate and evaporated. The oil obtained is dissolved in isopropyl ether, whereupon the solution is treated with hexane and left to stand in a refrigerator overnight. There is obtained rac-(2S*)-2-[(R*)-4-chloro-α-nitrobenzyl]cycloheptanone in the form of colourless crystals of m.p. 77°-78°.

(b) A solution of 12.8 g (43.3 mmol) of rac-(2S*)-2-[(R*)-4-chloro-α-nitrobenzyl]cycloheptanone in 160 ml of dry tetrahydrofuran is added dropwise to a suspension of 4.1 g (108.2 mmol) of lithium aluminium hydride in 120 ml of dry tetrahydrofuran under argon. The reaction mixture is stirred at 50° overnight, cooled, treated with tetrahydrofuran/water (1:1), the separated precipitate is filtered off under suction and the filtrate is evaporated. The residue is treated with water and extracted with ether. The organic phase is extracted with 3N hydrochloric acid; the aqueous phase is made alkaline by the addition of conc. ammonia and extracted with methylene chloride. The organic phase is washed with water, dried over magnesium sulphate and evaporated. The oil obtained is recrystallized from methylene chloride/hexane. There is obtained rac-(1S*)-cis-2-[(R*)-α-(aminomethyl)-4-chlorobenzyl]cycloheptanol in the form of colourless crystals of m.p. 92°-93°.

(c) 5.5 ml of 35 percent formaldehyde solution and 3 ml of 88 percent formic acid are added to a solution of 7.3 g (27.3 mmol) of rac-(1S*)-cis-2-[(R*)-α-(aminomethyl)-4-chlorobenzyl]cycloheptanol in 70 ml of dimethylformamide. The mixture is heated to 100° for 2 hours, the readily volatile constituents are distilled off in a water-jet vacuum at 75°, the residue is treated with water and conc. ammonia and extracted twice with 100 ml of methylene chloride each time. The organic phase is washed with water, dried over magnesium sulphate and evaporated. The oil obtained is chromatographed on a 10-fold amount of aluminium oxide while eluting with toluene. The oil obtained crystallizes upon treatment with hexane. The rac-(1S*)-cis-2-/(R*)-4-chloro-α-[(dimethylamino)methyl]benzyl/cycloheptanol obtained melts at 86°-87° and the hydrochloride obtained therefrom in the usual manner is recrystallized from ethanol/ether and melts at 254°-255°.

EXAMPLE 20

(a) A solution of 4.55 g (16.1 mmol) of (—)-(2S)-[(R)-4-chloro-α-(nitromethyl)benzyl]cyclohexanone [prepared according to Helv. Chim. Acta 65, 1637 (1982)] in 80 ml of dry tetrahydrofuran is added dropwise at room temperature while stirring to a suspension of 1.5 g (40.4 mmol) of lithium aluminium hydride in 50 ml of dry tetrahydrofuran under argon. The reaction mixture is stirred at room temperature overnight, treated with 20 ml of tetrahydrofuran/water (1:1), the separated precipitate is filtered off under suction while washing with methylene chloride and the filtrate is evaporated. The residue is dissolved in ether, the ethereal phase is extracted with 1N hydrochlorid acid, the acidic phase is made alkaline with 3N sodium hydroxide solution and extracted with methylene chloride. The organic phase is washed with water, dried over magnesium sulphate and evaporated. There is obtained (+)-(1S)-cis-2-[(R)-α-(aminomethyl)-4-chlorobenzyl]cyclohexanol in the form of a yellow oil ($[α]_D^{20}=+14.7°$, c=0.6 in chloroform), which is processed as such.

(b) A solution of 2.8 g of (+)-(1S)-cis-2-[(R)-α-(aminomethyl)-4-chlorobenzyl]cyclohexanol in a mixture of 60 ml of dimethylformamide, 2.2 ml of 35 percent formaldehyde solution and 1.5 ml of 88 percent formic acid is stirred at 100° for 2 hours, the readily volatile constituents are distilled off at 70° in a water-jet vacuum, the residue is treated with 3N sodium hydroxide solution and extracted with ether. The organic phase is washed with water, dried over magnesium sulphate and evaporated. The oil obtained is chromatographed on a 20-fold amount of aluminium oxide (activity grade II, neutral) while eluting with toluene, there being obtained a colourless oil which crystallizes upon treatment with isopropyl ether/hexane. There is obtained (—)-(1S)-cis-2-/(R)-4-chloro-α-[(dimethylamino)methyl]benzyl/cyclohexanol in the form of colourless crystals of m.p. 117°; $[α]_D^{20}==15.6°$ (c=1, chloroform).

EXAMPLE 21

(a) A solution of 26.5 g (117.8 mmol) of 1-(4'-benzyloxyphenyl)-2-nitroethylene in 350 ml of methylene chloride is cooled to —75° and treated dropwise while stirring within one hour with 25.3 g (129.6 mmol) of (—)-(S)-1-(1-cyclohexen-1-yl)-2-(methoxymethyl)pyrrolidine [Helv. Chim. Acta 65, 1637 (1982)]. The mixture is subsequently stirred at 0° for 1 hour and at room temperature overnight. The reaction mixture is cooled to 0° and treated with 15 minutes with 130 ml of 1N hydrochloric acid and stirred for 1 hour. The acidic phase is extracted twice with 150 ml of methylene chloride each time and the organic phase is washed with 100 ml of 1N hydrochloric acid and twice with 100 ml of water each time, dried over magnesium sulphate and freed from solvent. The oil obtained is chromatographed on a 10-fold amount of silica gel with methylene chloride. After crystallization from methylene chloride/isopropyl ether there is obtained (−)-(S)-2-[(R)-4-(benzyloxy)-α-(nitromethyl)benzyl]cyclohexanone in the form of colourless crystals of m.p. 168°–169°; $[α]_D^{20} = −19.8°$ (c=0.5, chloroform).

(b) A solution of 9.5 g of (−)-(S)-[(R)-4-(benzyloxy)-α-(nitromethyl)benzyl]cyclohexanone in 150 ml of dry tetrahydrofuran is added dropwise at room temperature while stirring to a suspension of 2.5 g (67.2 mmol) of lithium aluminium hydride in 80 ml of dry tetrahydrofuran under argon and the mixture is stirred at room temperature for 16 hours. The reaction mixture is treated with 20 ml of tetrahydrofuran/water (1:1), the separated precipitate is filtered off under suction while washing with methylene chloride and the filtrate is evaporated. The residue is dissolved in ether, the ethereal phase is extracted with 1N hydrochloric acid, the acidic phase is made alkaline with 3N sodium hydroxide solution and extracted with methylene chloride. The organic phase is washed with water, dried over magnesium sulphate and evaporated. There is obtained (+)-(1S)-cis-2-[(R)-α-(aminomethyl)-4-(benzyloxy)benzyl]cyclohexanol in the form of a colourless oil; $[α]_D^{20} = +14.7°$ (c=0.7, chloroform).

(c) A solution of 7.2 g of (+)-(1S)-cis-2-[(R)-α-(aminomethyl)-4-(benzyloxy)benzyl]cyclohexanol in a mixture of 100 ml of dimethylformamide, 4.4 ml of 35 percent formaldehyde solution and 2.5 ml of 88 percent formic acid is stirred at 100° for 2 hours, the readily volatile constituents are distilled off at 70° in a water-jet vacuum, the residue is treated with 3N sodium hydroxide solution and extracted with ether. The organic phase is washed with water, dried over magnesium sulphate and freed from solvent. The oil obtained is chromatographed on a 20-fold amount of aluminium oxide with toluene. There is obtained (−)-(1S)-cis-2-/(R)-4-(benzyloxy)-α-[(dimethylamino)methyl]benzyl/cyclohexanol in the form of colourless crystals of m.p. 128°–130°; $[α]_D^{20} = =13°$ (c=1, ethanol), (d) 3.0 g of (−)-(1S)-cis-2-/(R)-4-(benzyloxy)-α-[(dimethylamino)methyl]benzyl/cyclohexanol are dissolved in 100 ml of ethanol and, after the addition of 0.3 g of 5 percent palladium/carbon, hydrogenated at room temperature. After separating the catalyst the filtrate is concentrated and the crystalline residue is recrystallized from ethanol. There is obtained (−)-(1S)-cis-2-/(R)-α-[(dimethylamino)methyl]-4-hydroxybenzyl/cyclohexanol in the form of colourless crystals of m.p. 235°–237°; $[α]_D^{20} = −19.8°$ (c=1, ethanol).

EXAMPLE 22

(a) A solution of 35.75 g (158.7 mmol) of 1-(4'-benzyloxyphenyl)-2-nitroethylene in 450 ml of methylene chloride is cooled to 0° and treated dropwise within 1 hour while stirring with 34.1 g (174.6 mmol) of (+)-(R)-1-(1-cyclohexen-1-yl)-2-(methoxymethyl)pyrrolidine [Helv. Chim. Acta 65, 1637 (1982)]. The mixture is subsequently stirred at 0° for 3 hours and at room temperature overnight. The reaction mixture is cooled to 0° and treated within 15 minutes with 175 ml of 1N hydrochloric acid and stirred for 1 hour. The acidic phase is extracted twice with 150 ml of methylene chloride each time, the organic phase is washed with 100 ml of 1N hydrochloric acid and twice with 100 ml of water each time, dried over sodium sulphate and freed from solvent. The oil obtained is filtered on a 10-fold amount of silica gel with methylene chloride. After recrystallization from methylene chloride/isopropyl ether there is obtained (+)-(R)-2-[(S)-4-(benzyloxy)-α-(nitromethyl)benzyl]cyclohexanone in the form of colourless crystals of m.p. 159°–160°; $[α]_D^{20} = +22°$ (c=0.5, chloroform).

(b) A solution of 10.0 g of (+)-(R)-2-[(S)-4-(benzyloxy)-α-(nitromethyl)benzyl]cyclohexanone in 120 ml of dry tetrahydrofuran is added dropwise at room temperature while stirring to a suspension of 2.6 g (70.7 mmol) of lithium aluminium hydride in 80 ml of dry tetrahydrofuran under argon and the mixture is stirred at room temperature for 16 hours. The reaction mixture is treated with 20 ml of tetrahydrofuran/water (1:1) and 10 ml of conc. sodium hydroxide solution, the separated precipitate is filtered off under suction while washing with methylene chloride and the filtrate is evaporated. There is obtained crude (−)-(b 1R)-cis-2-[(S)-α-(aminomethyl)-4-(benzyloxy)benzyl]cyclohexanol in the form of a yellowish oil.

(c) A solution of 9.4 g of (−)-(1R)-cis-2-[(S)-α-(aminomethyl)-4-(benzyloxy)benzyl) cyclohexanol in a mixture of 130 ml of dimethylformamide, 5.6 ml of 35 percent formaldehyde solution and 3.3 ml of 88 percent formic acid is stirred at 100° for 2 hours, the readily volatile constituents are distilled off at 70° in a water-jet vacuum, the residue is treated with conc. ammonia and extracted with methylene chloride. The organic phase is washed twice with 50 ml of water each time, dried over sodium sulphate and the solvent is evaporated. The resulting oil (7.5 g) is chromatographed on a 20-fold amount of aluminium oxide with toluene. After crystallization from methylene chloride/hexane there is obtained (+)-(1R)-cis-2-/(S)-4-(benzyloxy)-α-[(dimethylamino)methyl]benzyl/cyclohexanol in the form of colourless crystals of m.p. 133°–134°; $[α]_D^{20} = +12.9°$ (c=1, ethanol).

(d) 2.6 g (7.35 mmol) of (+)-(1R)-cis-2-/(S)-4-(benzyloxy)-α-[(dimethylamino)methyl]benzyl/cyclohexanol are dissolved in 100 ml of ethanol and, after treatment with 250 mg of 5 percent palladium/carbon, hydrogenated at room temperature. After separating the catalyst the filtrate is concentrated and the crystals obtained are recrystallized from ethanol. There is obtained (+)-(1R)-cis-2-/(S)-α-[(dimethylamino)methyl]-4-hydroxybenzyl/cyclohexanol in the form of colourless crystals of m.p. 235°–236°; $[α]_D^{20} = +19.8°$ (c=1, ethanol).

EXAMPLE 23

(a) A solution of 50.0 g (195.9 mmol) of 4-(benzyloxy)-ω-nitrostyrene in 600 ml of methylene chloride is added at 0° within 45 minutes while stirring to a solution of 46.3 g (255.2 mmol) of 1-morpholino-1-cycloheptene in 350 ml of methylene chloride and the mixture is stirred at 0° for 3 hours and subsequently at room temperature overnight. The mixture is treated once more with 11.6 g (63.8 mmol) of 1-morpholino-1-cycloheptene, stirred at 0° for 5 hours and then treated rapidly with 300 ml of 1N hydrochloric acid while stirring intensively and stirred for 1 hour. The aqueous phase is separated and extracted twice with 300 ml of methylene chloride each time. The organic phase is washed with water, dried over sodium sulphate and evaporated. The oil obtained is purified on 500 g of silica gel while eluting with toluene. After recrystallization from isopropyl ether there is obtained rac-(S*)-2-[(R*)-4-(benzyloxy)-α-(nitromethyl)benzyl]cycloheptanone in the form of colourless crystals of m.p. 120°–121°

(b) A solution of 47.5 g (129.3 mmol) of rac-(S*)-2-[(R*)-4-(benzyloxy)-α-(nitromethyl)benzyl]cycloheptanone in 650 ml of dry tetrahydrofuran is added dropwise while stirring to a suspension of 12.2 g (323 mmol) of lithium aluminium hydride in 350 ml of dry tetrahydrofuran under argon so that the temperature does not exceed 40°. The mixture is stirred at 40° overnight, cooled, treated dropwise with 50 ml of tetrahydrofuran/water (1:1) and 50 ml of conc. sodium hydride solution, the separated precipitate is filtered off under suction while washing with methylene chloride and the filtrate is evaporated. The oily residue crystallizes upon treatment with isopropyl ether. There is obtained rac-[(2S*)-α-(aminomethyl)-4-(benzyloxy)benzyl]cycloheptanol in the form of colourless crystals of m.p. 150°–151°.

(c) A solution of 20.0 g (50.91 mmol) of rac-[(2S*)-α-(aminomethyl)-4-(benzyloxy)benzyl]cycloheptanol in 180 ml of dimethylformamide is stirred at 100° for 5 hours with 18 ml of 35 percent formaldehyde solution and 9.0 ml of 88 percent formic acid. After distilling off the readily volatile constituents at 70° in water-jet vacuum the residue is taken up in 200 ml of ether and extracted twice with 50 ml of 3N hydrochloric acid each time. The acidic phase is made alkaline with conc. sodium hydroxide solution and extracted twice with 350 ml of methylene chloride each time. The organic phase is washed twice with 100 ml of water each time, dried over magnesium sulphate and evaporated. The oil obtained crystallizes after dissolution in isopropyl ether. There are obtained 13.7 g of rac-(2S*)-/(R*)-4-(benzyloxy)-α-[(dimethylamino)methyl]benzyl/cycloheptanol in the form of colourless crystals of m.p. 106°–107°.

(d) 12.0 g of (2S)-/(R*)-4-(benzyloxy)-α-[(dimethylamino)methyl]benzyl/cycloheptanol are dissolved in 120 ml of ethanol and, after the addition of 1.2 g of 5 percent palladium/carbon, hydrogenated at room temperature. After separating the catalyst the filtrate is evaporated and the crystalline residue is recrystallized from methylene chloride/isopropyl ether. There is obtained rac-(2S*)-/(R*)-α-[(dimethylamino)methyl]-4-hydroxybenzyl/cycloheptanol in the form of colourless crystals of m.p. 197°–198°. The rac-(2S*)-/(R*)-α-[(dimethylamino)methyl]-4-hydroxybenzyl/cycloheptanol hydrochloride prepared in the usual manner crystallizes after treatment with ether and melts at 66°–68°.

EXAMPLE 24

(a) A solution of 27.5 g (272.5 mmol) of diisopropylamine and 250 ml of dry tetrahydrofuran is cooled to −78° and treated dropwise at this temperature within 30 minutes while stirring with 70 ml of a 1.6 molar butyl lithium/hexane solution (272.5 mmol). After 15 minutes there is added within 10 minutes a solution of 34.5 g (272.5 mmol) of cyclooctanone in 250 ml of dry tetrahydrofuran and the mixture is stirred at −78° for a further 1 hour. A solution of 50 g (272.5 mmol) of 4-chloro-ω-nitrostyrene in 500 ml of dry tetrahydrofuran is subsequently added within 45 minutes and the mixture is stirred at −78° for a further 2 hours. The reaction mixture is then treated with 27.5 ml of glacial acetic acid, the mixture is poured into 1 l of ice-water and extracted 3 times with 500 ml of methylene chloride each time. The organic phase is washed with water, dried over sodium sulphate and the solvent is distilled off. The resulting oil (90 g) is chromatographed on a 10-fold amount of silica gel with toluene. There is obtained rac-(2S*)-2-[4-chloro-α-(nitromethyl)benzyl]cyclooctanone in the form of a yellowish oil.

(b) A solution of 7.4 g (23.9 mmol) of rac-(2S*)-2-[4-chloro-α-(nitromethyl)benzyl]cyclooctanone in 100 ml of dry tetrahydrofuran is added dropwise at 40° while stirring to a suspension of 2.3 g (59.7 mmol) of lithium aluminium hydride in 75 ml of dry tetrahydrofuran under argon and the mixture is stirred under reflux temperature overnight. The mixture is cooled, excess lithium aluminium hydride is destroyed with tetrahydrofuran/water (1:1), the separated precipitate is filtered off under suction while washing with methylene chloride and the filtrate is evaporated. The residue is dissolved in ether, the ethereal phase is extracted with 1N hydrochloric acid, the acidic phase is made alkaline with conc. ammonia and extracted with methylene chloride. The organic phase is washed with water, dried over magnesium sulphate and evaporated. After crystallization from methylene chloride/isopropyl ether there is obtained rac-(2S*)-2-[(R*)-α-(aminomethyl)-4-chlorobenzyl]cyclooctanol in the form of colourless crystals of m.p. 110°–111°.

(c) A reaction of 3.0 g of rac-(2S*)-2-[(R*)-α-(aminomethyl)-4-chlorobenzyl]cyclooctanol in a mixture of 25 ml of dimethylformamide, 2.0 ml of 35 percent formaldehyde solution and 1.2 ml of 88 percent formic acid is stirred at 100° for 2 hours, the readily volatile constituents are distilled off at 70° in a water-jet vacuum, the residue is treated with conc. ammonia and extracted with methylene chloride. The organic phase is washed once with 50 ml of water, dried over sodium sulphate and the solvent is evaporated. The oil obtained is purified on a 10-fold amount of alumium oxide with toluene. After elution with toluene there is obtained rac-(2S*)-2-/(R*)-4-chloro-α-[(dimethylamino)methyl]benzyl/cyclooctanol in the form of a colourless oil which is converted into the hydrochloride in the usual manner. After crystallization from alcohol/ether there is obtained rac-(2S*)-2-/(R*)-4-chloro-α-[(dimethylamino)methyl]benzyl/cyclooctanol hydrochloride in the form of colourless crystals of m.p. 252°–253°.

EXAMPLE 25

(a) A solution of 20.0 g (109 mmol) of 4-chloro-ω-nitrostyrene in 300 ml of methylene chloride is added dropwise within about 30 minutes while stirring and cooling to 0° to a solution of 21.8 g (142 mmol) of N-(1-cyclopenten-1-yl)morpholine in 200 ml of methylene chloride and the mixture is stirred at 0° for a further 3 hours. The mixture is treated with 142 ml of 1N hydrochloric acid and stirred for a further 1 hour. The aqueous phase is separated and extracted twice with 100 ml of methylene chloride each time. The organic phase is washed with water, dried over sodium sulphate and the solvent is distilled off. After chromatography on silica gel there is eluted with toluene 2-[4-chloro-α-(nitromethyl)benzyl]cyclopentanone as a yellowish oil (diastereomeric mixture in the ratio 70:30).

(b) A solution of 14.2 g (53 mmol) of 2-[4-chloro-α-(nitromethyl)benzyl]cyclopentanone in 200 ml of dry tetrahydrofuran is added dropwise within 1 hour under argon to a suspension of 5.0 g (132.6 mmol) of lithium aluminium hydride in 150 ml of dry tetrahydrofuran and the mixture is heated to reflux overnight. After cooling excess lithium aluminium hydride is destroyed with tetrahydrofuran/water (1:1) and 25 ml of conc. sodium hydroxide solution, the separated precipitate is filtered off under suction and the solvent is distilled off. The resulting oil (11.25 g) is dissolved in 100 ml of dimethylformamide, treated with 9.5 ml of 37 percent formaldehyde solution and 5 ml of 88 percent formic acid and held at 100° for 2 hours. After cooling the readily volatile constituent is distilled of at 75° in a water-jet vacuum, the residue is treated with 3N sodium hydroxide solution and extracted with methylene chloride. The organic phase is washed with water, dried over sodium sulphate and evaporated. The oil obtained is chromatographed on a 30-fold amount of aluminium oxide with toluene. There is obtained oily 2-/4-chloro-α-[(dimethylamino)methyl]benzyl/cyclopentanol as a diastereomeric mixture in the ratio 3:1. The 2-/4-chloro-α-[(dimethylamino)methyl]benzyl/cyclopentanol hydrochloride prepared in the usual manner is crystallized from alcohol/ether and melts at 228°–230°.

EXAMPLE A

Tablets of the following composition, having a breakbar, are manufactured in the usual manner.

| Ingredients: | mg/tablet |
|---|---|
| rac-(1S*)—cis-2-/(R*)—4-Chloro-α-[(dimethylamino)methyl]benzyl/-cyclohexanol | 50.0 |
| Lactose | 102.0 |
| Maize starch | 45.0 |
| Talc | 10.4 |
| Magnesium stearate | 2.6 |
| Tablet weight | 210.0 |

We claim:

1. A compound of the formula

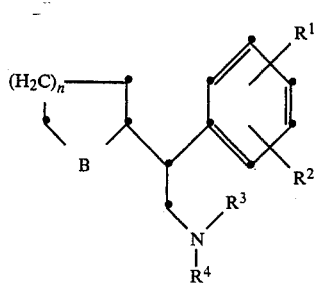

wherein $R^1$ and $R^2$ each signify hydrogen, halogen, trifluoromethyl, lower alkoxy, lower alkyl, hydroxy or nitro, with the proviso that at least one of $R^1$ and $R^2$ is different from hydrogen, $R^3$ and $R^4$ each signify lower alkyl, n signifies the number 1, 2, 3 or 4 and B signifies the group —CO— or —CHOH—, and pharmaceutically acceptable acid addition salts thereof.

2. A compound as defined in claim 1, wherein n signifies the number 1, 2 or 3.

3. A compound as defined in claim 2 wherein n is 2.

4. A compound as defined in claim 3 wherein B is the group —CHOH.

5. A compound as defined in claim 4 wherein $R^3$ and $R^4$ are methyl.

6. A compound as defined in claim 1, with the relative configuration depicted in formula Ia or Ib and the corresponding optically uniform enantiomeric forms:

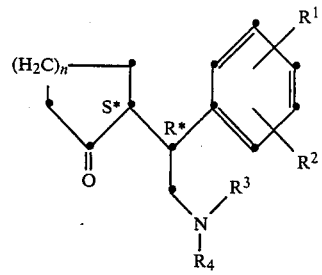

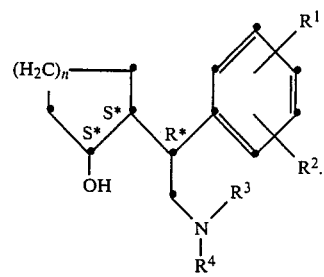

7. A compound as defined in claim 6 wherein either $R^1$ signifies halogen, lower alkoxy or hydroxy and $R^2$ signifies hydrogen of $R^1$ and $R^2$ in each case both signify halogen, lower alkoxy or hydroxy.

8. A compound as defined in claim 7, wherein n signifies the number 2.

9. A compound as defined in claim 8, wherein B signfies the group —CHOH—.

10. A compound as defined in claim 9, wherein $R^3$ and $R^4$ signify methyl.

11. A compound as defined in claim 1 of the formula rac-(1S*)-cis-2-/(R*)-4-Chloro-α-[(dimethylamino)methyl]benzyl/cyclohexanol.

12. A compound as defined in claim 1 of the formula rac-(1S*)-cis-2-(R*)-α-[(Dimethylamino)methyl]-4-hydroxybenzyl/cyclohexanol.

13. A compound as defined in claim 1 of the formula (1S)-cis-2-/(R)-4-Chloro-α-[(dimethylamino)methyl]benzyl/cyclohexanol.

14. A compound as defined in claim 1 of the formula (1R)-cis-2-/(S)-4-Chloro-α-[(dimethylamino)methyl]benzyl/cyclohexanol.

15. A compound as defined in claim 1 of the formula rac-(1S*)-cis-2-/(R*)-3,4-Dichloro-α-[(dimethylamino)methyl]benzyl/cyclohexanol.

16. A compound as defined in claim 1 of the formula rac-(1S*)-cis-2-/(R*)-4-Methoxy-α-[(dimethylamino)methyl]benzyl/cyclohexanol.

17. A compound as defined in claim 1 of the formula rac-(1S*)-cis-2-/(R*)-α-[(Dimethylamino)methyl]-3,4-[dimethoxybenzyl]cyclohexanol.

18. A compound as defined in claim 1 of the formula rac-(2S*)-2-/(R*)-4-Chloro-α-[(dimethylamino)methyl]benzyl/cyclohexanone.

19. A compound as defined in claim 1 of the formula (1S)-cis-2-/(R)-α-[(Dimethylamino)methyl]-4-hydroxylbenzyl/cyclohexanol.

20. A compound of the formula

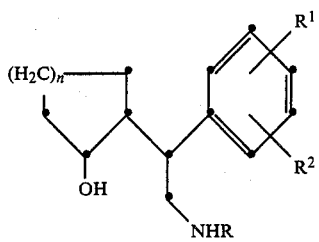

wherein $R^1$ and $R^2$ each signify hydrogen, halogen, trifluoromethyl, lower alkoxy, lower alkyl, hydroxy or nitro, with the proviso that at least one is different from hydrogen, R signifies hydrogen or lower alkyl and n signifies the number 1, 2, 3 or 4.

21. A compound as in claim 20 wherein n is 2.

22. A compound as defined in claim 21 wherein R is methyl.

23. A compound as in claim 22 wherein $R^1$ and $R^2$ are selected from the group consisting of hydrogen, halogen, lower alkoxy or hydroxy.

24. A compound of the formula

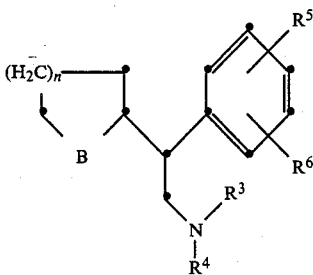

wherein $R^3$ and $R^4$, each signify lower alkyl, n signifies the number 1, 2, 3 or 4, B signifies the group —CO— or —CHOH—, and one of the residues $R^5$ and $R^6$ represents a protected hydroxyl group and the other represents hydrogen, halogen, trifluoromethyl, lower alkoxy, lower alkyl, nitro or a protected hydroxyl group, with the proviso that the term protected hydroxyl group does not signify lower alkoxy.

25. A compound as in claim 24 wherein n is 2.

26. A compound of the formula

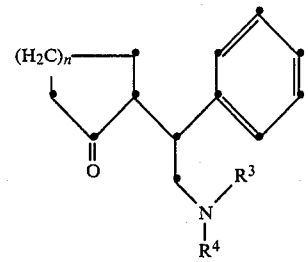

wherein $R^3$ and $R^4$ each signify lower alkyl and n signifies the number 1, 2, 3 or 4.

27. A compound as in claim 26 wherein n is 2.

28. A compound as defined in claim 27 wherein $R^3$ and $R^4$ are methyl.

29. A pharmaceutical composition containing a compound of the formula

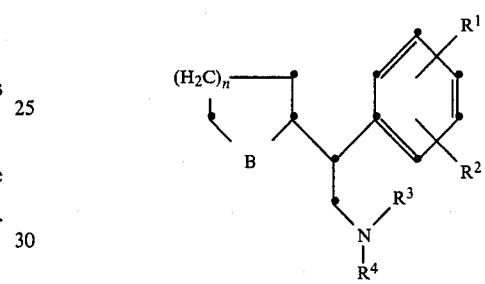

wherein $R^1$ and $R^2$ each signify hydrogen, halogen, trifluoromethyl, lower alkoxy, lower alkyl, hydroxy or nitro, with the proviso that at least one of $R^1$ and $R^2$ is different from hydrogen, $R^3$ and $R^4$ each signify lower alkyl, n signifies the number 1, 2, 3 or 4 and B signifies the group —CO— or —CHOH—, and a therapeutically or prophylatically inert excipient.

30. A method of treating depression or pain which comprises administering an effective amount of a compound of the formula

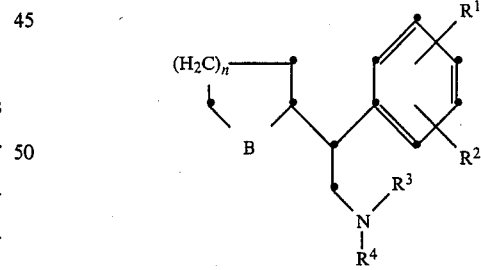

wherein $R^1$ and $R^2$ each signify hydrogen, halogen, trifluoromethyl, lower alkoxy, lower alkyl, hydroxy or nitro, with the proviso that at least one of $R^1$ and $R^2$ is different from hydrogen, $R^3$ and $R^4$ each signify lower alkyl, n signifies the number 1, 2, 3 or 4 and B signifies the group —CO— or —CHOH—, to a warm blooded animal suffering from depression or pain.

* * * * *